(12) United States Patent
Bunker et al.

(10) Patent No.: US 6,265,399 B1
(45) Date of Patent: Jul. 24, 2001

(54) CERTAIN BENZOTHIAZINE DIOXIDE ENDOTHELIN ANTAGONISTS AND PROCESSES FOR THEIR PREPARATION

(75) Inventors: Amy Mae Bunker, Middletown, CT (US); Xue-Min Cheng, Ann Arbor, MI (US); Annette Marian Doherty, Paris (FR); Jeremy John Edmunds, Ypsilanti, MI (US); Gerald David Kanter, West Bloomfield, MI (US); Chitase Lee, Ann Arbor, MI (US); Joseph Thomas Repine, Ann Arbor, MI (US); Richard William Skeean, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/445,504

(22) PCT Filed: Aug. 13, 1998

(86) PCT No.: PCT/US98/16856

§ 371 Date: Dec. 8, 1999

§ 102(e) Date: Dec. 8, 1999

(87) PCT Pub. No.: WO99/12916

PCT Pub. Date: Mar. 18, 1999

Related U.S. Application Data

(60) Provisional application No. 60/058,111, filed on Sep. 5, 1997, and provisional application No. 60/092,326, filed on Jul. 9, 1998.

(51) Int. Cl.[7] ..................... C07D 279/02; C07D 417/04; A61K 31/54
(52) U.S. Cl. ........................... 514/226.5; 544/49
(58) Field of Search ............................ 544/49; 514/226.5

(56) References Cited

FOREIGN PATENT DOCUMENTS

WO 96/26195 * 8/1996 (WO).

* cited by examiner

*Primary Examiner*—John M. Ford
*Assistant Examiner*—Hong Liu
(74) *Attorney, Agent, or Firm*—Elizabeth M Anderson; Charles W. Ashbrook

(57) ABSTRACT

The instant invention is a series of benzothiazine dioxides, or a pharmaceutically acceptable salt thereof, which are potent endothelin A antagonists with profound in vitro activity, and improved syntheses for the Formula 1

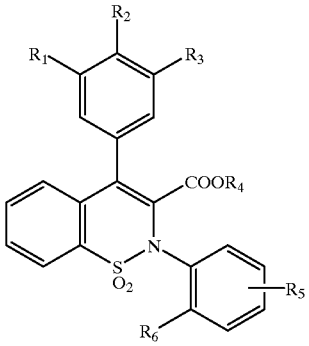

The compounds are useful in treating elevated levels of endothelin, essential renovascular malignant and pulmonary hypertension, cerebral infarction, cerebral ischemia, congestive heart failure, and subarachnoid hemorrhage.

13 Claims, No Drawings

CERTAIN BENZOTHIAZINE DIOXIDE ENDOTHELIN ANTAGONISTS AND PROCESSES FOR THEIR PREPARATION

CROSS-REFERENCE TO RELATED APPLICATIONS

This is a 371 filing of PCT/US98/16856 filed Aug. 13, 1998; priority is based on Provisional Application No. 60/058,111 filed Sep. 5, 1997, and Provisional Application No. 60/092,326 filed Jul. 9, 1998.

BACKGROUND OF THE INVENTION

The present invention relates to improved syntheses of known and novel benzothiazine dioxide which are potent and selective endothelin antagonists. The processes of the instant invention are improved over those recited in U.S. Pat. No. 5,599,811 which is hereby incorporated by reference.

The compounds of the instant invention exhibit very significant improvements over those described in U.S. Pat. No. 5,599,811. These improvements include: binding affinity to the $ET_A$ receptor, $ET_A$ selectivity, functional activity, long pharmacokinetic half-life, high bioavailability, in vivo activity in inhibiting the pressor effect caused by bET-1, oral activity with relatively long duration of action, and efficacy in acute hypoxic pulmonary hypertension in rats.

The processes of the instant invention provide more facile syntheses with higher yields. They are short, clean, reproducible and no tedious chromatography is needed. Moreover, the processes are scaleable and therefore useful for large-scale development.

The present invention also relates to antagonists of endothelin useful as pharmaceutical agents, to pharmaceutical compositions which include these compounds and a pharmaceutically acceptable carrier, and to pharmaceutical methods of treatment. More particularly, the compounds of the present invention are antagonists of endothelin useful in treating elevated levels of endothelin, acute and chronic renal failure, essential renovascular malignant and pulmonary hypertension, cerebral infarction and cerebral ischemia, cerebral vasospasm, cirrhosis, septic shock, congestive heart failure, endotoxic shock, subarachnoid hemorrhage, arrhythmias, asthma, preeclampsia, atherosclerotic disorders including Raynaud's disease and restenosis, angina, cancer, benign prostatic hyperplasia, ischemic disease, gastric mucosal damage, hemorrhagic shock, ischemic bowel disease, and diabetes.

Also, the compounds will be useful in cerebral ischemia or cerebral infarction resulting from a range of conditions such as thromboembolic or hemorrhagic stroke, cerebral vasospasm, head injury, hypoglycemia, cardiac arrest, status epilepticus, perinatal asphyxia, anoxia such as from drowning, pulmonary surgery, and cerebral trauma.

SUMMARY OF THE INVENTION

This invention is improved processes for the preparation of compounds of Formula 1

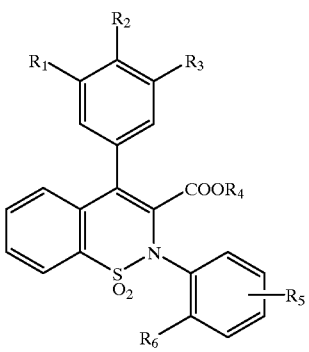

or a pharmaceutically acceptable salt thereof wherein $R_1$ is hydrogen, alkyl, or alkoxy;

$R_2$ is hydrogen or alkoxy;

$R_3$ is alkyl or alkoxy;

$R_2$ and $R_3$ may be joined to form a ring

$R_4$ is hydrogen or alkyl;

$R_5$ is hydrogen, alkyl, alkoxy, halogen at the 2 or 3, or 4, or 5 positions or $R_5$ is a 3,4-methylenedioxo; and $R_6$ is $CF_3$, halogen, alkyl, benzyl, phenyl, hydroxy, or pyrrole comprising:

a) alkylating a compound of formula A

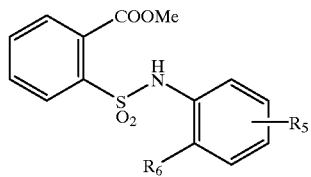

using sodium hydride in DMF followed by reaction with methyl bromoacetate to produce a compound of formula B

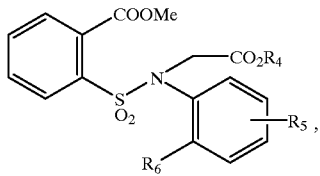

b) combining compound B in THF with a solution of $TiCl_4$ in solvent at −78° C., treating with triethylamine and quenching with an acid to produce a compound of formula C

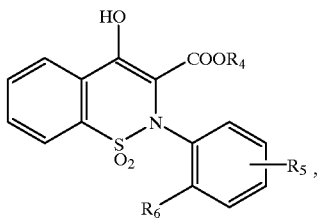

C c) treating compound C with triflic anhydride in a solvent in the presence of pyridine for from 1 to 5 hours to produce a compound of formula D

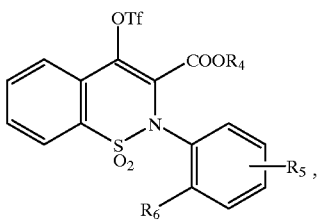

D d) coupling the compound D with a boronic acid of formula X

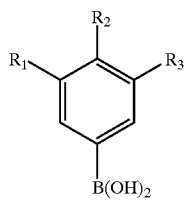

X in DMF and toluene in the presence of a palladium catalyst and potassium carbonate at about 100° C. to produce a compound of Formula 1.

The free acid of Formula 1 is obtained by sponification of the ester with, for example, LiOH in THF/MeOH or in dioxane. Any strongly alkaline solution in methanol can be used.

Compounds of the invention are those prepared by the above process, especially those selected from:

4-(3,5-Dimethoxy-phenyl)-2-(2-trifluoromethyl-phenyl)-1,1-dioxo-1,2-dihydro-1$\lambda^6$-benzo[e][1,2]thiazine-3-carboxylic acid;

2-(2-Chloro-phenyl)-4-(3,5-dimethoxy-phenyl)-1,1-dioxo-1,2-dihydro-1$\lambda^6$-benzo[e][1,2]thiazine-3-carboxylic acid;

2-(2-Bromo-phenyl)-4-(3,5-dimethoxy-phenyl)-1,1-dioxo-1,2-dihydro-1$\lambda^6$-benzo[e][1,2]thiazine-3-carboxylic acid;

2-(2-Chloro-phenyl)-4-(7-methoxy-benzo[1,3]dioxol-5-yl)-1,1-dioxo-1,2-dihydro-1$\lambda^6$-benzo[e][1,2]thiazine-3-carboxylic acid;

2-(2-Benzyl-phenyl)-4-(7-methoxy-benzo[1,3]dioxol-5-yl)-1,1-dioxo-1,2-dihydro-1$\lambda^6$-benzo[e][1,2]thiazine-3-carboxylic acid;

2-(2,6-Dimethyl-phenyl)-4-(7-methoxy-benzo[1,3]dioxol-5-yl)-1,1-dioxo-1,2-dihydro-1$\lambda^6$-benzo[e][1,2]thiazine-3-carboxylic acid monosodium salt;

4-(7-Methoxy-benzo[1,3]dioxol-5-yl)-1,1-dioxo-2-(2-trifluoromethylphenyl)-1,2-dihydro-1$\lambda^6$-benzo[e][1,2]thiazine-3-carboxylic acid;

4-Benzo[1,3]dioxol-5-yl-1,1-dioxo-2-(2-trifluoromethyl-phenyl)-1,2-dihydro-1$\lambda^6$-benzo[e][1,2]thiazine-3-carboxylic acid;

4-Benzo[1,3]dioxol-5-yl-2-(2-ethyl-phenyl)-1,1-dioxo-1,2-dihydro-1$\lambda^6$-benzo[e][1,2]thiazine-3-carboxylic acid;

4-Benzo[1,3]dioxol-5-yl-2-(2-propyl-phenyl)-1,1-dioxo-1,2-dihydro-1$\lambda^6$-benzo[e][1,2]thiazine-3-carboxylic acid;

4-Benzo[1,3]dioxol-5-yl-2-(2-isopropyl-phenyl)-1,1-dioxo-1,2-dihydro-1$\lambda^6$-benzo[e][1,2]thiazine-3-carboxylic acid;

4-Benzo[1,3]dioxol-5-yl-2-(2-butyl-phenyl)-1,1-dioxo-1,2-dihydro-1$\lambda^6$-benzo[e][1,2]thiazine-3-carboxylic acid;

4-Benzo[1,3]dioxol-5-yl-2-(2-fluoro-phenyl)-1,1-dioxo-1,2-dihydro-1$\lambda^6$-benzo[e][1,2]thiazine-3-carboxylic acid;

4-Benzo[1,3]dioxol-5-yl-2-(2-hydroxy-phenyl)-1,1-dioxo-1,2-dihydro-1$\lambda^6$-benzo[e][1,2]thiazine-3-carboxylic acid;

4-Benzo[1,3]dioxol-5-yl-2-(2,3-dichloro-phenyl)-1,1-dioxo-1,2-dihydro-1$\lambda^6$-benzo[e][1,2]thiazine-3-carboxylic acid;

4-Benzo[1,3]dioxol-5-yl-2-(2,4-dichloro-phenyl)-1,1-dioxo-1,2-dihydro-1$\lambda^6$-benzo[e][1,2]thiazine-3-carboxylic acid;

4-Benzo[1,3]dioxol-5-yl-2-(2-chloro-4-methoxy-phenyl)-1,1-dioxo-1,2-dihydro-1$\lambda^6$-benzo[e][1,2]thiazine-3-carboxylic acid;

4-Benzo[1,3]dioxol-5-yl-2-(3-chloro-2-methyl-phenyl)-1,1-dioxo-1,2-dihydro-1$\lambda^6$-benzo[e][1,2]thiazine-3-carboxylic acid;

4-Benzo[1,3]dioxol-5-yl-2-(2,6-dimethyl-phenyl)-1,1-dioxo-1,2-dihydro-1$\lambda^6$-benzo[e][1,2]thiazine-3-carboxylic acid;

4-Benzo[1,3]dioxol-5-yl-1,1-dioxo-2-(2-pyrrol-1-yl-phenyl)-1,2-dihydro-1$\lambda^6$-benzo[e][1,2]thiazine-3-carboxylic acid;

4-Benzo[1,3]dioxol-5-yl-2-(3,4-dimethyl-isoxazol-5-yl)-1,1-dioxo-1,2-dihydro-1$\lambda^6$-benzo[e][1,2]thiazine-3-carboxylic acid;

4-(6-Methoxy-benzo[1,3]dioxol-5-yl)-1,1-dioxo-2-(2-trifluoromethylphenyl)-1,2-dihydro-1$\lambda^6$-benzo[e][1,2]thiazine-3-carboxylic acid; and 4-(3,5-Dimethyl-phenyl)-2-(2-trifluoromethyl-phenyl)-1,1-dioxo-1,2-dihydro-1$\lambda^6$-benzo[e][1,2]thiazine-3-carboxylic acid.

The invention is also a process for the preparation of a compound of Formula 1

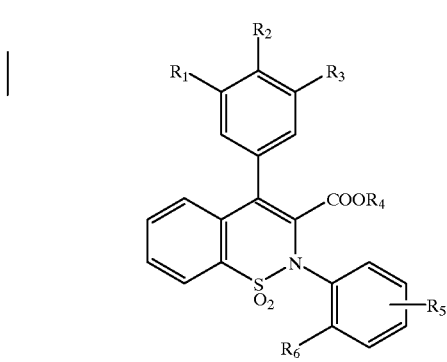

comprising:

a) treating aryl bromide with n-butyl lithium followed by zinc bromide to generate an aryl zinc bromide of Formula Y

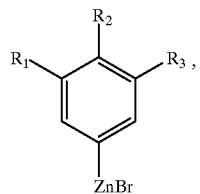

b) reacting the product of step a) above with

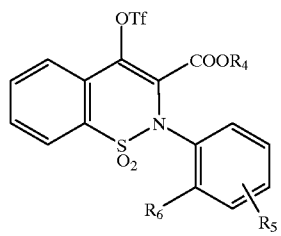

in THF in the presence of a palladium catalyst to produce a compound of Formula 1

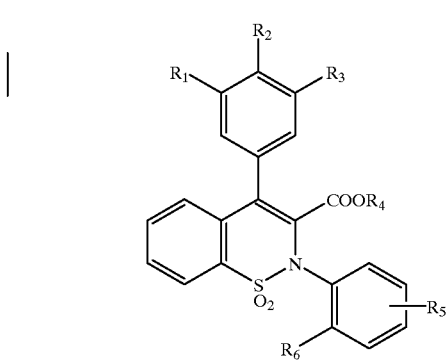

The free acid of Formula 1 is obtained by sponification of the ester.

The following three compounds are obtained by the above process:

2-(2-Bromo-phenyl)-4-(7-methoxy-benzo[1,3]dioxol-5-yl)-1,1-dioxo-1,2-dihydro-1$\lambda^6$-benzo[e][1,2]thiazine-3-carboxylic acid monosodium salt;

4-(7-Ethyl-benzo[1,3]dioxol-5-yl)-1,1-dioxo-2-(2-trifluoromethyl-phenyl)-1,2-dihydro-1$\lambda^6$-benzo[e][1,2]thiazine-3-carboxylic acid, potassium salt; and 4-Benzo[1,3]dioxol-5-yl-2-(2-benzyl-phenyl)-1,1-dioxo-1,2-dihydro-1$\lambda^6$-benzo[e][1,2]thiazine-3-carboxylic acid.

The invention is also a process for the preparation of a compound of formula B

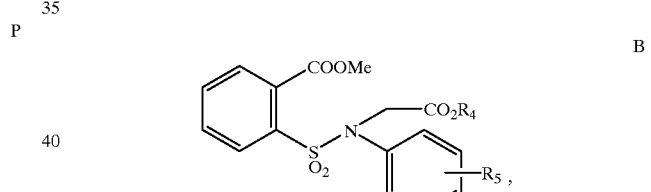

comprising:

a) reacting a phenyl sulfonyl chloride with 1 equivalent of aniline to produce a sulfonamide of formula F

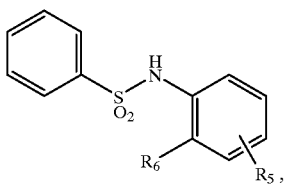

F b) lithiating the product of step a) above at low temperatures and quenching with $CO_2$ to form a compound of formula G

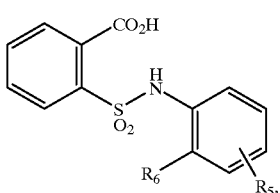

G c) treating the product of step b) above with acetic anhydride and a catalytic amount of methanesulfonic acid to produce a compound of formula H

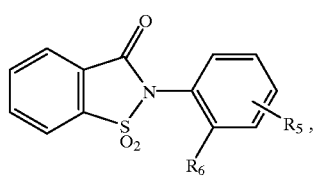

H d) treating the product of step c) above with NaOMe followed by methyl bromoacetate to produce a compound B as above.

Compound B is carried over to Formula 1 as described before.

Compounds of the invention are those prepared from the above process, especially 4-(7-Ethyl-benzo[1,3]dioxol-5-yl)-1,1-dioxo-2-(2-trifluoromethyl-phenyl)-1,2-dihydro-1$\lambda^6$-benzo[e][1,2]thiazine-3-carboxylic acid methyl ester.

The sodium and potassium salts of the above compound are preferred.

The invention is also a process for the preparation of a compound of Formula 1 which comprises

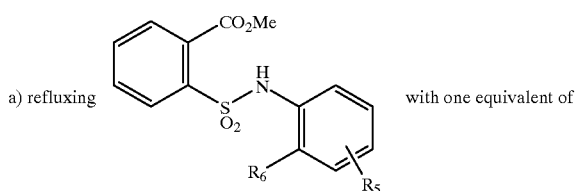

A a) refluxing                with one equivalent of with one equivalent of pyridine and DMAP to produce cyclic intermediate of formula H

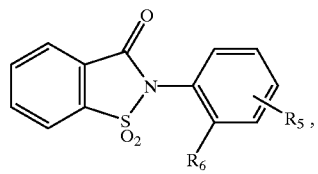

H b) treating the product of Step a) above with potassium hexamethyldisilylazide followed by t-butyl acetate in THF to produce the keto ester of formula I

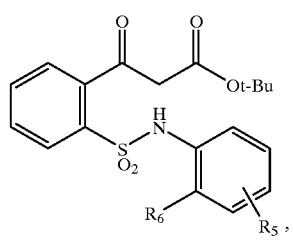

I c) brominating the product from Step b) above to produce an intermediate of formula J

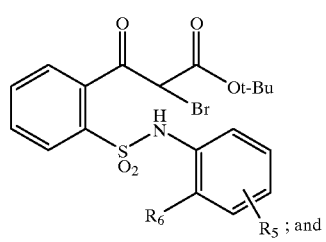

J d) cyclizing the product of Step c) above using potassium carbonate in DMF to produce enol of formula K

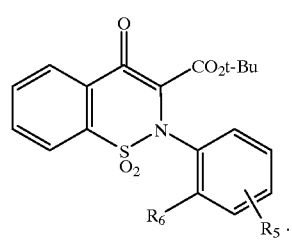

K

The enol is then used to produce a compound of Formula 1 above.

Compounds of the invention are those prepared by the above process and especially those selected from:

2-(6-Methyl-benzo[1,3]dioxol-5-yl)-4-hydroxy-1,1-dioxo-1,2-dihydro-1$\lambda^6$-benzo[e][1,2]thiazine-3-carboxylic acid tert-butyl ester;

2-(2-Bromo-phenyl)-4-hydroxy-1,1-dioxo-1,2-dihydro-1$\lambda^6$-benzo[e][1,2]thiazine-3-carboxylic acid tert-butyl ester;

2-(2-Chloro-phenyl)-4-hydroxy-1,1-dioxo-1,2-dihydro-1$\lambda^6$-benzo[e][1,2]thiazine-3-carboxylic acid tert-butyl ester; and 2-(6-Chloro-benzo[1,3]dioxol-5-yl)-4-hydroxy-1,1-dioxo-1,2-dihydro-λ⁶-benzo[e][1,2]thiazine-3-carboxylic acid tert-butyl ester.

The invention is also a process for the preparation of a compound of Formula 1 comprising:

a) reacting 2-methylanaline with benzenesulfonyl chloride to produce a compound of formula F

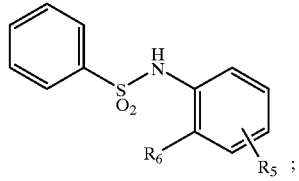

b) treating the product of step a) above with n-butyl lithium and then with 3-methoxy-4,5-methylenedioxybenzaldehyde to produce a compound of formula M

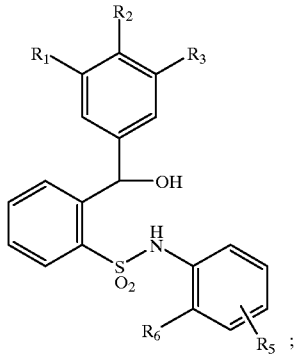

c) treating the product of step b) above with sodium hydride followed by methyl bromoacetate to produce a compound of formula N

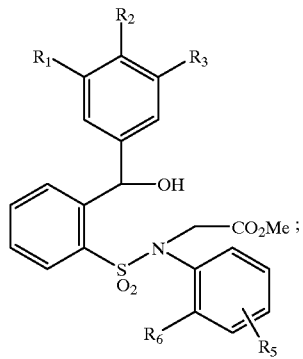

d) oxidizing the product of step c) above to produce the corresponding keto ester of formula O

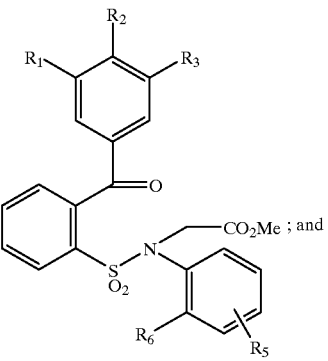

e) cyclizing the product of step d) above by treating with a base or a Lewis acid in an appropriate solvent to produce the corresponding ester of Formula 1

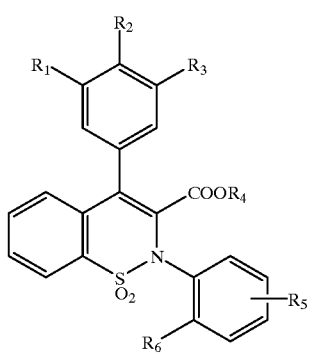

Compounds of the invention are those prepared by the above process, especially 4-(7-Methoxy-benzo[1,3]dioxol-5-yl)-1,1-dioxo-2-o-tolyl-1,2-dihydro-1λ⁶-benzo[e][1,2]thiazine-3-carboxylic acid methyl ester.

The invention is also a pharmaceutical composition of the compounds of Formula 1 above comprising a therapeutically effective amount of a compound of Formula 1 in admixture with a pharmaceutically acceptable carrier.

The compounds of the invention are useful in inhibiting elevated levels of endothelin comprising administering to a host in need thereof a therapeutically effective amount of a compound of Formula 1 in unit dosage form. They are also useful in treating subarachnoid hemorrhage, essential, renovascular, malignant and pulmonary hypertension, congestive heart failure, cerebral ischemia, or cerebral infarction.

DETAILED DESCRIPTION OF THE INVENTION

In the compounds of Formula 1, the term "alkyl" means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, allyl, n-pentyl, n-hexyl, n-heptyl, n-octyl, n-nonyl, n-decyl, undecyl, and dodecyl.

"Halogen" is fluorine, chlorine, bromine or iodine.

The term "alkoxy" is an alkyl group as described above attached by oxygen to the rest of the molecule. Preferred alkoxy group are from 1 to 4 carbon atoms.

The host receiving a compound of the invention is a mammal, particularly a human.

The compounds of Formula 1 above may be prepared by several methods. These methods are illustrated in Schemes 1 through 3 and in a detailed manner by way of illustration in the example section of the specification.

Scheme 1 illustrates the general procedure for the preparation of the compounds of Formula 1. Synthesis of the intermediate A was described in U.S. Pat. No. 5,599,811. Reaction of methyl-2-(chlorosulfonyl)benzoate with an aniline in methylene chloride with 1 to 2 equivalents of pyridine and a catalytic amount of DMAP at room temperature overnight affords the sulfonamide A. The reaction can also be run using neat pyridine as the solvent. Alkylation of A was achieved by treatment of A with sodium hydride in DMF followed by reaction with methyl bromoacetate to give intermediate B. B can be converted to the key intermediate C via Claisen cyclization which were found to be promoted by at least two different catalysts. In condition I, the intermediate B in methylene chloride was added to a solution of 2 equivalents of $TiCl_4$ in methylene chloride at $-78°$ C. followed by the treatment with 2.2 equivalents of triethyl amine. The reaction was quenched with 1N HCl followed by aqueous work up and recrystallization. The condition II is similar to condition I with the use of 1.2 equivalents of $TiCl_2(OTf)_2$ (*Bull. Chem. Soc. Jpn,* 1989;62:1917) followed by quench with pH 7 phosphate buffer and extractive workup. The cyclized enol C was treated with triflic anhydride in solvents such as methylene chloride in the presence of 2 to 5 equivalents of pyridine for 1 to 5 hours to afford the triflate D quantitatively. The coupling reaction was carried out between the triflate D and the corresponding boronic acid in DMF and toluene (ratio of 1:4) in the presence of 10 mole % tetrakis(triphenyl phosphine)palladium as the catalyst and 1 to 2 equivalents of potassium carbonate under reflux for 2 hours. The reaction mixture was filtered, and the product was purified by column chromatography or by recrystallization. The free acid of the Formula 1 was obtained by sponification of the ester with aqueous LiOH in THF/MeOH or in dioxane. The free acid can be converted, for example, to a sodium or potassium salts, which are much more soluble in $H_2O$, by treating it with one equivalent of NaOH or KOH in MeOH followed by recrystallization.

Scheme 1a indicates an alternative assembly reaction for the formation of the 4-aryl benzothiazine derivatives exemplified by intermediate E. The coupling reaction was conducted by reacting an aryl zinc bromide, prepared by treating an aryl bromide with one equivalent of n-butyl lithium in THF followed by zinc bromide, with the intermediate D in the presence of 10% tetrakis(triphenylphosphine)palladium as the catalyst under reflux for 2 hours.

The Scheme 1 was further modified to replace a relatively expensive starting material, methyl-2-(chlorosulfonyl)benzoate, with phenyl sulfonyl chloride. The process (Scheme 1b) is proven to be more economical and workable in large scale. The sulfonamide F was formed by reacting the phenyl sulfonyl chloride with one equivalent of aniline under similar condition as described for A or using an equal amount of saturated sodium bicarbonate solution in THF. It was lithiated with n-BuLi at low temperature and quenched with $CO_2$ to form the intermediate G in 92% yield. The acid G was then treated with acetic anhydride with a catalytic amount of methanesulfonic acid to form the intermediate H. This cyclic compound was treated with NaOMe followed by quenching with methyl bromoacetate to form B directly in 71% yield.

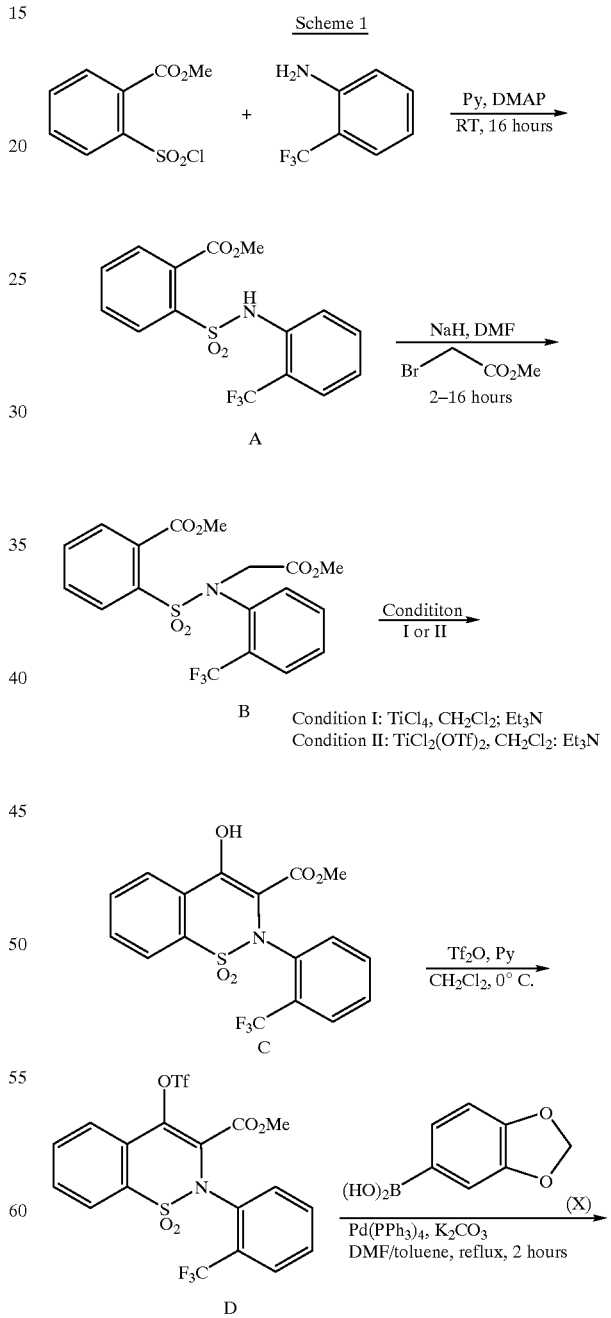

Scheme 1

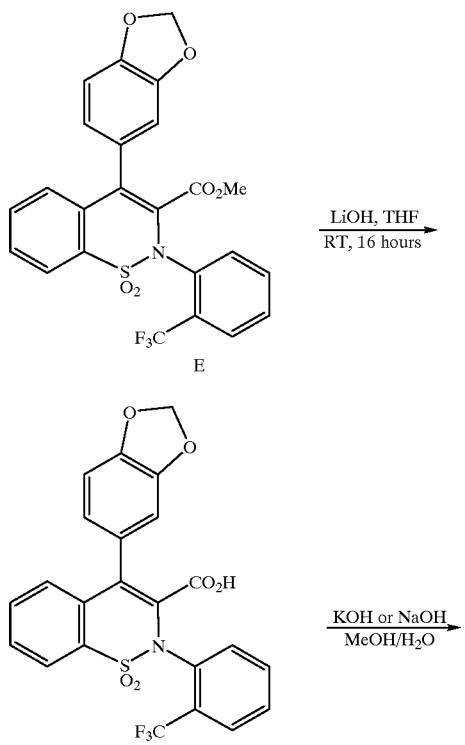
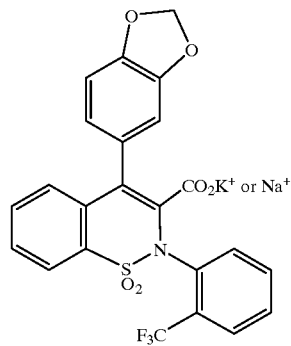
Scheme 1a
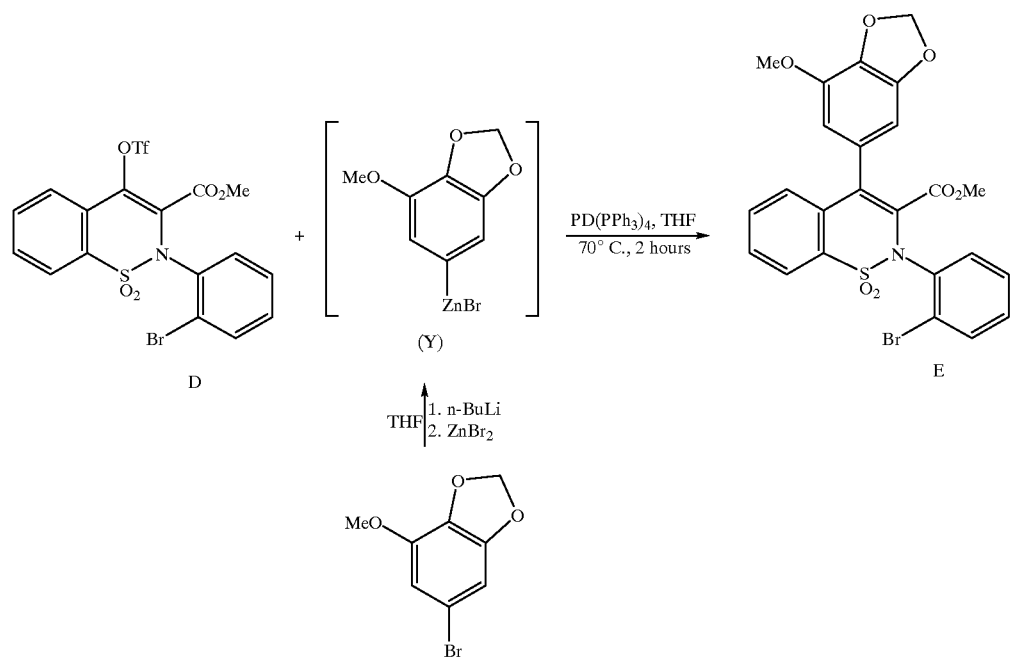

-continued
Scheme 1b

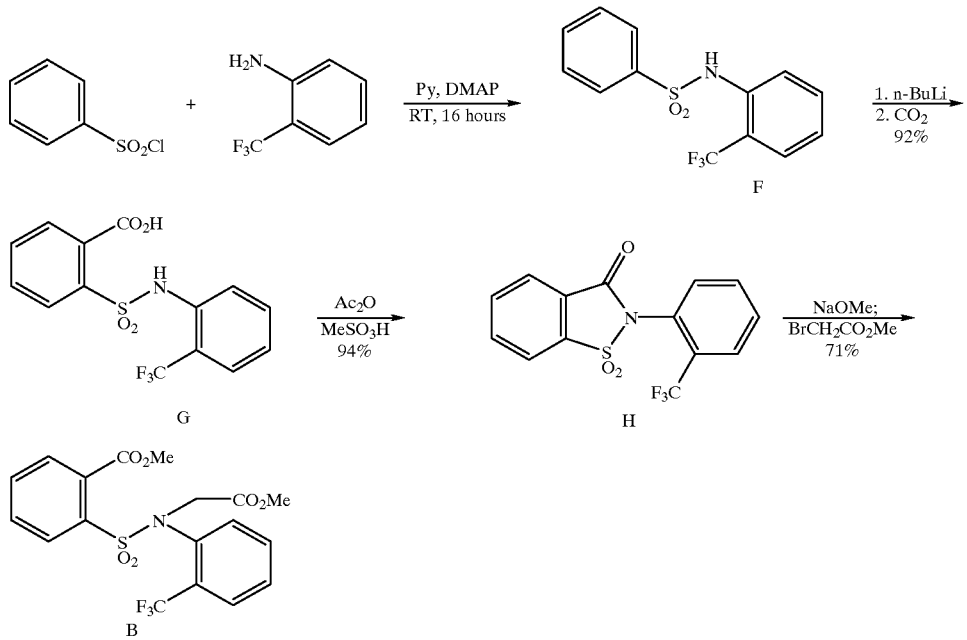

Several compounds in the Examples were synthesized through a synthesis outlined in Scheme 2. Compound A, obtained as described in Scheme 1 was refluxed in xylene for 16 hours with 1 equivalent of pyridine and a catalytic amount of DMAP to afford the cyclic intermediate H. This compound was treated with potassium hexamethyldisilylazide followed by t-butyl acetate in THF at −78° C. to yield the keto ester I. Bromination of I was carried out with NBS in carbon tetrachloride to obtain J which is in turn cyclized via treatment with potassium carbonate in DMF. The enol K was converted to the ester L with similar procedures illustrated in Scheme 1. Finally, the t-butyl ester was removed by treatment with TFA in methylene chloride at room temperature to give the free acid.

Scheme 2

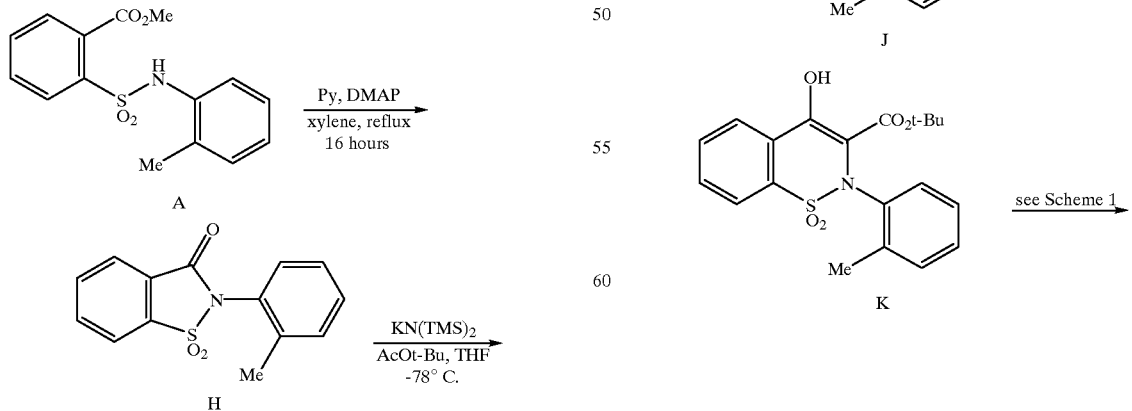

-continued

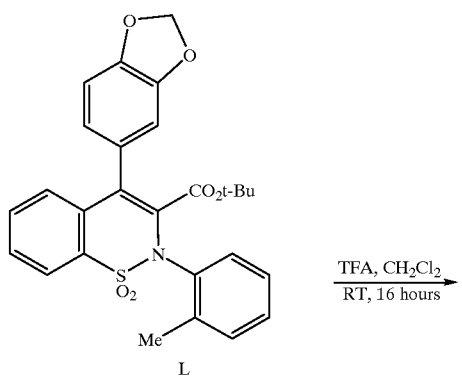

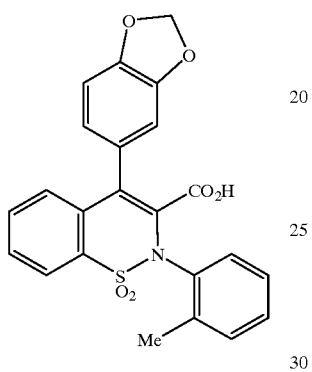

Scheme 3 illustrates an alternative synthesis that has been successfully utilized in the synthesis of certain analogs. This is illustrated by the synthesis of Example 8. Intermediate F was treated with 2 equivalents of n-butyl lithium at −78° C. to generate the dianion. Then a solution of 3-methoxy-4,5-methylenedioxybenzaldehyde in tetrahydrofuran was added to the reaction mixture. It was then warmed to 0° C. over 1.5 hours. Aqueous work up afforded M which was treated with sodium hydride followed by methyl bromoacetate to give N. Jones oxidation of N was carried out in acetone to afford the keto ester O in 60% yield. The cyclization of O can be promoted by a base or a Lewis acid such as titanium bis-chloro-bis-triflate in an appropriate solvent such as methylene chloride. The ester E was purified by column chromatography to provide pure sample in 53% yield. The esters synthesized through this route were sponified according to procedures described in Scheme 1.

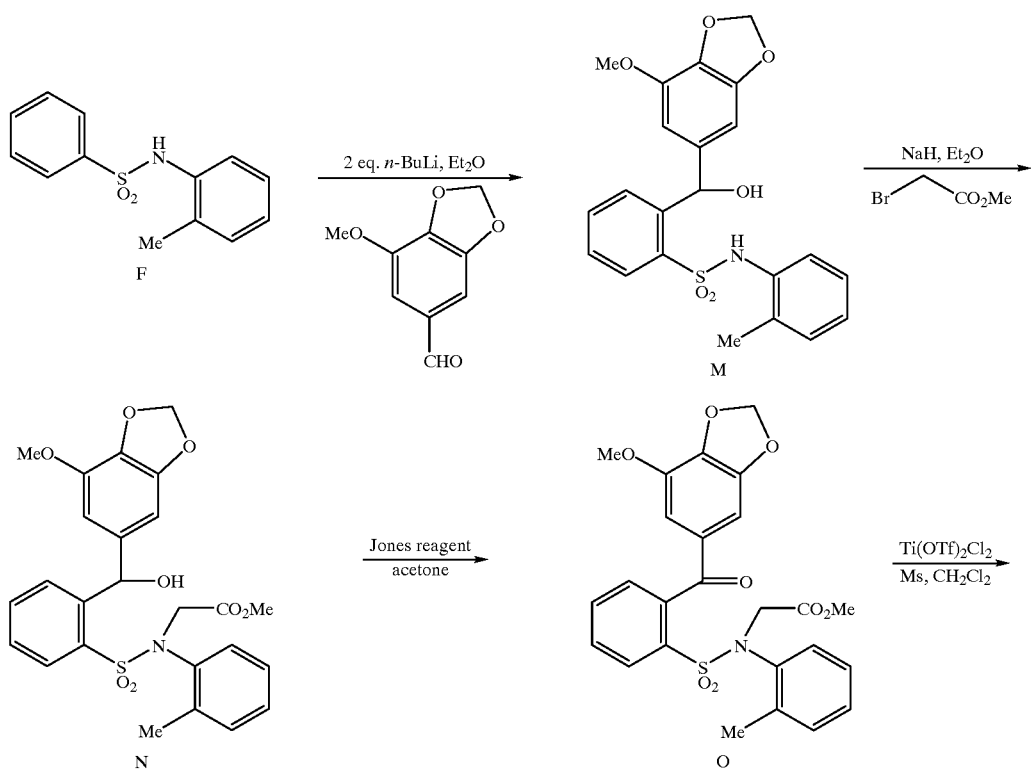

Scheme 3

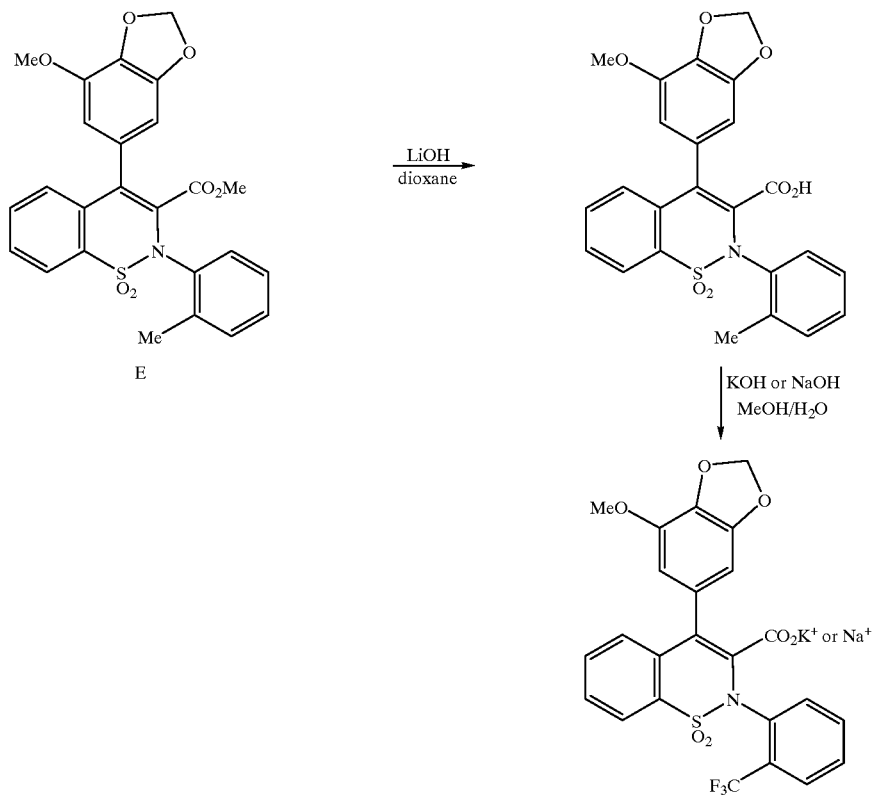

Some of the compounds of Formula 1 are capable of further forming both pharmaceutically acceptable base salts. All of these forms are within the scope of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S M, et al., "Pharmaceutical Salts," *Journal of Pharmaceutical Science*, 1977;66:1–19).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R or S configuration. The present invention includes all enantiomeric and epimeric forms as well as the appropriate diastereomeric mixtures thereof.

Test Protocols

The compounds of Formula 1 are valuable antagonists of endothelin. The tests employed indicate that compounds of the invention possess endothelin antagonist activity. Thus, the compounds were tested for their ability to inhibit $[^{125}I]$-ET-1($[^{125}I]$Endothelin-1) binding in a receptor assay. Selected compounds were also tested for antagonist activity by inhibition of ET-1 stimulated arachidonic acid release and ET-1 stimulated vasoconstriction. The following testing procedures were used (Doherty A M, et al., "Design of C-Terminal Peptide Antagonists of Endothelin: Structure-Activity Relationships of ET-1 [16-21, D-His $^{16}$]", *Bioorganic and Medicinal Chemistry Letters*, 1993 ;3:497–502).

Radioligand Binding Assays

The following cultured cells were used in binding experiments: Ltk⁻cells expressing recombinant human $ET_AR$ ($HET_A$), and CHO-K1 cells expressing recombinant human $ET_BR$ ($HET_B$).

Membranes were prepared from cultured cells by lysing cells in cold lysis buffer (5 mM HEPES, 2 mM EDTA, pH 7.4) and homogenizing with a Dounce "A" homogenizer. The homogenate was centrifuged at 30,000×g for 20 minutes at 40° C. Membrane pellets were suspended in cold buffer containing 20 mM Tris, 2 mM EDTA, 200 μM Pefabloc, 10 μM phosphoramidon, 10 μM leupeptin, 1 μM pepstatin at pH 7.4 and frozen at −80° C. until use. Membranes were thawed and homogenized with a Brinkmann Polytron then diluted in tissue buffer containing 20 mM Tris, 2 mM EDTA, 200 μM Pefabloc, and 100 μM bacitracin (pH 7.4). Radioligand and competing ligands were prepared in binding buffer containing 20 mM Tris, 2 mM EDTA, and 0.1% BSA.

Competing binding assays were initiated by combining membranes, [125I]-ET-1 (40 pM) and the competing ligand in a final volume of 250 μL and incubating for 2 hours at 37° C. The assay was terminated by filtration over Whatman GF/B filters which were presoaked with 50 mM Tris, pH 7.4 containing 0.2% BSA and 100 μM bacitracin. Nonspecific binding was defined as binding in the presence of 100 nM ET-1.

In Vitro Inhibition of ET-1 Stimulated Arachidonic Acid Release (AAR) in Cultured Rabbit Vascular Smooth Muscle Cells ($ET_A$) by the Compounds of the Invention Antagonist activity is measured by the ability of added compounds to reduce endothelin-stimulated arachidonic acid release in cultured vascular smooth muscle cells. [$^3$H] Arachidonic Acid Loading Media (LM) is DME/F12+0.5% FCS×0.25 mCi/mL [$^3$H] arachidonic acid (Amersham). Confluent monolayers of cultured rabbit renal artery vascular smooth muscle cells were incubated in 0.5 mL of the LM over 18 hours, at 37° C., in 5% $CO_2$. The LM was aspirated and the cells were washed once with the assay buffer (Hank's BSS+10 mM HEPES+fatty acid-free BSA (1 mg/mL)), and incubated for 5 minutes with 1 mL of the prewarmed assay buffer. This solution was aspirated, followed by an additional 1 mL of prewarmed assay buffer, and further incubated for another 5 minutes. A final 5-minute incubation was carried out in a similar manner. The same procedure was repeated with the inclusion of 10 μL of the test compound (1 nM to 1 μM) and 10 μL ET-1(0.3 nM) and the incubation was extended for 30 minutes. This solution was then collected, 10 mL of scintillation cocktail was added, and the amount of [$^3$H] arachidonic acid was determined in a liquid scintillation counter.

In Vitro Antagonism of ET-1 Stimulated Vasoconstriction ($VERA_A$) in the Rabbit Femoral Artery ($ET_A$) and Sarafotoxin 6C Stimulated Vasoconstriction in the Rabbit Pulmonary Artery ($ET_B$)

Male New Zealand rabbits were killed by cervical dislocation and exsanguination. Femoral and pulmonary arteries were isolated, cleaned of connective tissue, and cut into 4-mm rings. The endothelium was denuded by placing the rings over hypodermic tubing (32 gauge for femoral rings and 28 gauge for pulmonary rings, Small Parts, Inc., Miami, Fla.) and gently rolling them. Denuded rings were mounted in 20 mL organ baths containing Krebs-bicarbonate buffer (composition in mM: NaCl, 118.2; $NaHCO_3$, 24.8; KCl, 4.6; $MgSO_4$ $7H_2O$, 1.2; $KH_2PO_4$, 1.2; $CaCl_2$ $2H_2O$; Ca—$Na_2$ EDTA, 0.026; dextrose, 10.0), that was maintained at 37° C. and gassed continuously with 5% $CO_2$ in oxygen (pH 7.4). Resting tension was adjusted to 3.0 g for femoral and 4.0 g pulmonary arteries; the rings were left for 90 minutes to equilibrate. Vascular rings were tested for lack of functional endothelium (i.e., lack of an endothelium-dependent relaxation response to carbachol (1.0 nM) in norepinephrine (0.03 nM) contracted rings. Agonist peptides, ET-1 (femoral), and S6c (pulmonary), were cumulatively added at 10-minute intervals. The ET antagonists were added 30 minutes prior to adding the agonist.

Inhibition of bET-1 Induced Pressor Effect in Rat

Male Sprague-Dawley (Charles River Laboratories, Kingston, Ontario, Canada) weighing 250 to 350 g are anesthetized (Inactin, 120 mg/kg, I.P.) and acutely instrumented with a carotid artery catheter to monitor arterial blood pressure and with a jugular vein catheters to administer intravenous drugs. Once instrumented, the rats are ganglionic-blocked with mecamylamine (1.25 mg/kg, I.V.) to prevent hemodynamic reflexes and then challenged with big endothelin-1 (bET-1) (1.0 nmol/kg, I.V.). The peak arterial pressor response in rats pre-treated with selected compounds of invention compared to vehicle-treated rats is used to determine activity expressed as % inhibition. For I.V. activity selected compounds of invention was dose 10 minutes before the bET-1 challenge, and for oral activity selected compounds of invention was administered via oral gavage 8 or 24 hours before the bET-1 challenge.

TABLE 1

Example/Structure

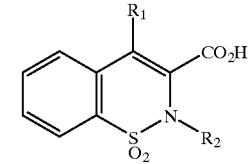

| Example | $R_1$ | $R_2$ |
|---|---|---|
| 1 | 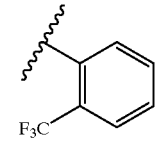 | 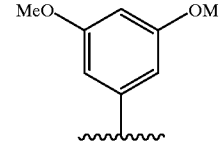 |
| 2 | 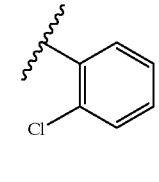 | 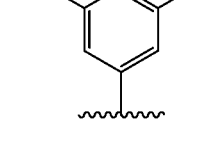 |
| 3 | 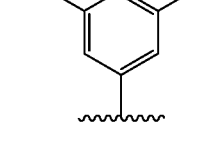 | 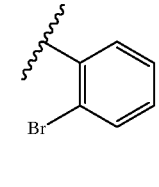 |
| 4 | 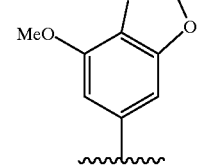 | 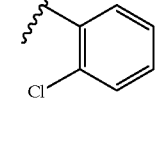 |

TABLE 1-continued

Example/Structure

![Structure with R1, CO2H, N-R2, SO2 on benzothiazine]

| Example | R1 | R2 |
|---|---|---|
| 5 | 7-MeO-benzo[1,3]dioxol-5-yl | 2-benzylphenyl |
| 6 | 7-MeO-benzo[1,3]dioxol-5-yl | 2,6-dimethylphenyl |
| 7 | 7-MeO-benzo[1,3]dioxol-5-yl | 2-(CF3)phenyl |
| 8 | 7-MeO-benzo[1,3]dioxol-5-yl | 2-Me-phenyl |
| 9 | 7-MeO-benzo[1,3]dioxol-5-yl | 2-Br-phenyl |
| 10 | 7-Et-benzo[1,3]dioxol-5-yl | 2-(CF3)phenyl |
| 11 | benzo[1,3]dioxol-5-yl | 2-(CF3)phenyl |
| 12 | benzo[1,3]dioxol-5-yl | 2-Me-phenyl |
| 13 | benzo[1,3]dioxol-5-yl | 2-Et-phenyl |
| 14 | benzo[1,3]dioxol-5-yl | 2-(n-Pr)-phenyl |
| 15 | benzo[1,3]dioxol-5-yl | 2-(i-Pr)-phenyl |
| 16 | benzo[1,3]dioxol-5-yl | 2-(n-Bu)-phenyl |

TABLE 1-continued

Example/Structure

![Structure with R1, CO2H, N-R2, S O2]

| Example | R1 | R2 |
|---------|----|----|
| 17 | benzo[1,3]dioxol-5-yl | 2-bromophenyl |
| 18 | benzo[1,3]dioxol-5-yl | 2-chlorophenyl |
| 19 | benzo[1,3]dioxol-5-yl | 2-fluorophenyl |
| 20 | benzo[1,3]dioxol-5-yl | 2-hydroxyphenyl |
| 21 | benzo[1,3]dioxol-5-yl | 2,3-dichlorophenyl |
| 22 | benzo[1,3]dioxol-5-yl | 2,4-dichlorophenyl |
| 23 | benzo[1,3]dioxol-5-yl | 3-chloro-4-methoxyphenyl |
| 24 | benzo[1,3]dioxol-5-yl | 3-chloro-2-methylphenyl |
| 25 | benzo[1,3]dioxol-5-yl | 6-chlorobenzo[1,3]dioxol-5-yl |
| 26 | benzo[1,3]dioxol-5-yl | 2,6-dimethylphenyl |
| 27 | benzo[1,3]dioxol-5-yl | 2-(pyrrol-1-yl)phenyl |
| 28 | benzo[1,3]dioxol-5-yl | 3,4-dimethylisoxazol-5-yl |

TABLE 1-continued

Example/Structure

[Structure: benzene-fused sulfonamide ring with R₁, CO₂H, N-R₂, SO₂]

| Example | R₁ | R₂ |
|---|---|---|
| 29 | [benzodioxole] | [2-benzylphenyl] |
| 30 | [methoxy-benzodioxole, MeO-] | [2-CF₃-phenyl] |
| 31 | [3,5-dimethoxyphenyl, MeO- / -OMe] | [2-Cl-phenyl] |

TABLE 2

ET Receptor Binding and Functional Activities

| Example | HET$_A$ (IC$_{50}$, µM) | HET$_B$ (IC$_{50}$, µM) | AAR$_A$ (IC$_{50}$, µM) | VERA$_A$ (pA$_2$) |
|---|---|---|---|---|
| 1 | 0.003 | >2.5 | | 6.6 |
| 2 | 0.002 | 7.3 | | 6.8 |
| 3 | 0.003 | >2.5 | | |
| 4 | 0.003 | 5.6 | | |
| 5 | 0.004 | 2 | | |
| 6 | 0.004 | >2.5 | | 7.1 |
| 7 | 0.003 | 2.5 | 0.0045 | 7.0 |
| 8 | 0.008 | 3.9 | | 6.5 |
| 9 | 0.002 | >2.5 | | 6.9 |
| 10 | 0.0006 | 2.2 | | 7.7 |
| 11 | 0.011 | 11 | | 6.6 |
| 12 | 0.061 | >25 | 0.1 | |
| 13 | 0.023 | >2.5 | | |
| 14 | 0.035 | >2.5 | | 5.8 |
| 15 | 0.09 | 11 | | |
| 16 | 0.026 | >2.5 | | |
| 17 | 0.03 | >25 | 0.031 | 6.0 |
| 18 | 0.036 | >25 | 0.032 | 5.8 |
| 19 | 0.11 | >25 | | |
| 20 | 0.06 | >2.5 | | |
| 21 | 0.03 | 13 | | |
| 22 | 0.05 | 13 | | |
| 23 | 0.021 | 6.2 | | |
| 24 | 0.03 | 17 | | |
| 25 | 0.11 | >25 | 0.05 | 6.0 |
| 26 | 0.017 | >25 | | |
| 27 | 0.04 | 19 | | |
| 28 | 0.09 | >25 | | |
| 29 | 0.04 | >2.5 | | |
| 30 | 0.095 | >2.5 | | |
| 31 | 0.006 | >2.5 | | 5.7 |

For example, Example 10 is a potent inhibitor (IC$_{50}$=0.6 nM) of ET-1 binding to human ETA receptors. It also has potent functional antagonist activity in human pulmonary artery smooth muscle cells blocking ET-1 induced Ca++ transients via the ETA receptor (IC$_{50}$=0.2 nM). it exhibits antagonism to ET-1 stimulated vasoconstriction in rabbit femoral artery with pA$_2$ value of 7.7. In vivo, ET$_A$ blockade with oral Example 10 was demonstrated through inhibition of bET-1 pressor response in the rat (10 mg/kg produced 44% inhibition at 8 hours postdose and 30 mg/kg produced a 48% inhibition at 24 hours postdose) and dog (15 mg/kg produced 25% inhibition at 24 hours postdose).

Oral Example 10 inhibited acute hypoxic pulmonary hypertension in the rat in a dose dependent manner with the ED$_{50}$=0.8 mg/kg (the plasma EC$_{50}$=0.046 µg/mL). Example 10 was well absorbed orally both in rat and dog. Terminal elimination t½'s were determined to be 8.5 and 2.2 hours in rat and dog, respectively, and bioavailability is 77% and 100% in rat and dog.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula 1 or a corresponding pharmaceutically acceptable salt of a compound of Formula 1.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, table, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists of endothelin, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the preferred methods for preparing the compounds of the invention.

EXAMPLE 1A

Following are prepared according to Scheme 1.

2-(2-Trifluoromethyl-phenylsulfamoyl)-benzoic Acid Methyl Ester

Methyl 2-(chlorosulfonyl)benzoate (23.5 g, 0.1 mol) was dissolved in 150 mL of anhydrous pyridine in a 500 mL flask. Catalytic amount of DMAP (4-dimethylaminopyridine) (0.04 eq) was added. 2-Trifluoromethylaniline (20 g, 0.12 mol) was added to the reaction mixture, and it was allowed to stir at room temperature overnight. Pyridine was removed, and the residue was diluted with 250 mL of EtOAc. It was then washed with 1N HCl solution followed by brine. After drying with $MgSO_4$, the EtOAc was removed in vacuo to give a thick red oil. The crude product was recrystallized from hexane/$Et_2O$ to give the product 1A as white crystals (17.63 g, 49% yield).

Analysis calculated for $C_{15}H_{12}F_3N_1O_4S_1$: C, 50.14; H, 3.37; N, 3.90. Found: C, 50.02; H, 3.28; N, 3.82.

MS (CI) M/E 359.8 ($M^+$)

EXAMPLE 1B

2-[Methoxycarbonylmethyl-(2-trifluoromethyl-phenyl)-sulfamoyl]-benzoic Acid Methyl Ester To the suspension of NaH (60% in mineral oil, 2.0 g, 50 mmol) in 45 mL of DMF at 0° C. was added a solution of 2-(2-trifluoromethyl-phenylsulfamoyl)-benzoic acid methyl ester (12.0 g, 33.3 mmol) in 22 mL of DMF dropwise. After about 10 minutes, 11.22 g (66.8 mmol) of methyl bromoacetate was added, and reaction solution was warmed to room temperature in 3 hours. The light yellow reaction mixture was poured into ice water. The mixture was then extracted with EtOAc 3×(~400 mL) and washed with brine. The organic layer was dried over $MgSO_4$ and evaporated down to a sick light orange oil. White crystals were formed upon treatment with $Et_2O$ and hexane. It was collected and dried over the vacuum oven to give pure 2-[methoxycarbonylmethyl-(2-trifluoromethyl-phenyl)-sulfamoyl]-benzoic acid methyl ester (13.85 g, 96%).

MS (CI) M/E 431.7 ($M^+$)

Alternative procedure: To dimethylformamide (220 mL) was added 2-(2-trifluoromethyl-phenylsulfamoyl)-benzoic acid methyl ester, (8.0 g, 22.2 mmol). After cooling to 0° C., a solution of potassium hexamethyl-disilazide (0.5 M, 44.5 mL) in toluene was added. Methyl bromoacetate (4.32 mL, 45.6 mmol) was added, followed by stirring at 70° C. overnight. The solvent was evaporated in vacuo, and the residue was suspended in ethyl ether and washed with saturated sodium bicarbonate, brine, and 1N citric acid solutions. The ether was dried over anhydrous magnesium sulfate, filtered, and evaporated to give a crystalline solid, 5.59 g, 58% yield. NMR spectra and elemental analysis were consistent with the structure.

Compound 1B can also be synthesized using procedures outlined in Scheme 1b with benzenesulfonyl chloride. Following is the experimental detail:

a. Preparation of 1F: N-(2-Trifluoromethyl-phenyl)-benzenesulfonamide

Benzenesulfonyl chloride (400 g, 2.26 moles) was dissolved in dichloromethane (2 L). To this was added o-trifluoromethylaniline (250 mL, 320 g, 1.99 mol), pyridine (222 mL), and DMAP (7.5 g). The resulting solution was stirred at room temperature for 3 days (72 h), then heated to reflux for 1 hour. The cooled solution was then concentrated on the rotary evaporator, with the bath temperature gradually raised to 70° C. The residue was taken up in ether (3 L) and 1N HCl (1.5 L). The ether layer was separated, washed 2×500 mL with 1N HCl, 1×1 L with brine, 1×1 L with saturated sodium bicarbonate, and once more with 1 L of brine. It was then dried over magnesium sulfate, filtered with suction, and concentrated on the rotary evaporator without heat. The product formed fine crystals as the ether evaporated, and when most of the ether was gone, the crystals were slurried with hexane (2 L), collected with suction and dried. Yield 571 g, 84%.

b. Preparation of 1G: 2-(2-Trifluoromethyl-phenylsulfamoyl)-benzoic Acid

A 22-L flask was equipped with an overhead stirrer, nitrogen inlet and thermocouple, and placed in an acetone bath. The flask was charged with 1F (544.5 g, 1.807 mol) and THF (10 L, from freshly opened bottles) and stirred. When a solution had formed, dry ice was added to the bath until the temp was <–70° C. n-Butyllithium (2.4 L of 1.6M, 3.84 mol) was added in portions, keeping the temperature below –55° C. (30 minutes). The reaction mixture was then stirred at –70° C. to –72° C. for 3 hours, then bone-dry carbon dioxide was bubbled in, keeping the temperature below –55° C. This was continued until no further exotherm was observed, then about 10 minutes longer. The mixture was then warmed to room temperature over 1 hour, transferred to a rotary evaporator, and stripped at 50° C. until no more THF came off. The residue was dissolved in water (5 L), and the basic solution was washed with 3×1 L ether. The solution was then acidified by addition of 330 mL concentrated HCl. The acid product was extracted from the aqueous layer with 3×1 L ether. The combined ether layers were dried over magnesium sulfate, filtered, and stripped on the rotary evaporator. The solid residue was broken up and agitated with hot tap water (4 L, at about 60° C.) for 20 minutes, then collected with suction and dried in vacuo (1 mm Hg) for 24 hours. Yield: 575 g, 92%. This material contained traces amount of impurities, which were removed in the next step.

c. Preparation of 1H: 1,1-Dioxo-2-(2-trifluoromethyl-phenyl)-1,2-dihydro-1$\lambda^6$-benzo[d]isothiazol-3-one Compound 1G (300 g, 0.876 moles) was slurried in acetic anhydride (350 mL). Methanesulfonic acid (3 drops) was added, and the resulting mixture was heated to reflux for 20 minutes. The resulting solution was allowed to stand without further heating for 30 minutes, then the apparatus was rearranged for distillation, and 190 mL of distillate was removed. The pot residue had begun to precipitate solids even at the boiling point, and 20 mL of the distillate was added back to improve workability of the mixture. The solids were broken up carefully as the mixture cooled, and heptane (100 mL) was added, followed by ether (~50 mL). The product was collected with suction, and washed with several small portions of ether (~150 mL total). Yield 266 g, 94%.

d. Preparation of 1B from 1H

Compound 1H (244 g, 0.745 mol) was added to a solution of sodium methoxide freshly prepared from 19 g (0.83 mol) of sodium and 600 mL methanol in a 3N 3-L round bottom flask equipped with a reflux condenser under nitrogen. The mixture was stirred for 30 minutes without further heating, at which point a greenish-yellow solution had formed. Methyl bromoacetate (83 mL, 137 g, 0.9 moles) was added, and the mixture was stirred without heat for 15 minutes, then heated to reflux for 90 minutes. The mixture was then cooled to 0° C., and the resulting ppt was collected with suction, washed 2×75 mL with ether, then 4×200 mL with water. The product was dried in vacuo (1 mm Hg) 2 hours at 60° C. Yield 228 g. 71%.

EXAMPLE 1C

4-Hydroxy-1,1-dioxo-2-(2-trifluoromethyl-2-phenyl)-1,2-dihydro-1$\lambda^6$benzo[e][1,2]thiazine-3-carboxylic Acid Methyl Ester In a 250 mL dry RB flask, 4.50 mL of TiCl$_4$ (40.8 mmol) was dissolved in 100 mL of CH$_2$Cl$_2$ and was cooled to –30° C. A solution of 2-[methoxycarbonyl-methyl-(2-trifluoromethyl-phenyl)-sulfamoyl]-benzoic acid methyl ester (8.0 g, 18.54 mmol) in 50 mL CH$_2$Cl$_2$ was added dropwise. The resulting solution was kept at –30° C. for 30 minutes and was then cooled to –78° C. Et$_3$N (7.75 mL, 55.6 mmol) in 50 mL CH$_2$Cl$_2$ was slowly syringed in resulting a dark red solution. The reaction mixture was stirred at –78° C. for 4 hours and was then poured into a 1-L flask containing 250 mL of Et$_2$O, 100 mL concentrated HCl, and 100 mL of H$_2$O. The mixture was stirred at room temperature overnight. The layers were separated, and the organic layer was washed with brine and dried over MgSO$_4$. Upon evaporation of the solvent, light yellowish crystals of 4-hydroxy-1,1-dioxo-2-(2-trifluoromethyl-phenyl)-1,2-dihydro-1$\lambda^6$benzo[e][1,2]thiazine-3-carboxylic acid methyl ester were formed. The product was collected through filtration and dried in oven to provide 2.2 g, 86% yield.

Analysis calculated for $C_{15}H_{12}F_3N_1O_4S_1$: C, 50.12; H, 3.74; N, 3.25; Found: C 50.04; H, 3.76; N, 3.11.

EXAMPLE 1D 1,1-Dioxo-4-(trifluoro-methanesulfonyloxy)-2-(2-trifluoromethyl-phenyl)-1,2-dihydro-1$\lambda^6$benzo[e][1,2]thiazine-3-carboxylic Acid Methyl Ester To dichloromethane (150 mL) was added 4-hydroxy-1,1-dioxo-2-(2-trifluoromethyl-phenyl)-1,2-dihydro-1$\lambda^6$-benzo

[e][1,2]thiazine-3-carboxylic acid methyl ester, (13.1 g, 32 mmol). After cooling to 0° C., pyridine (12.8 mL, 158 mmol) was added, followed by trifluoroacetic anhydride (10.7 g, 38 mmol). The mixture was stirred 30 minutes and allowed to warm to 25° C., then was poured into ethyl acetate (200 mL). The mixture was washed with brine, dried over anhydrous magnesium sulfate, filtered, and evaporated to a solid. Recrystallization from ethyl acetate and ethyl ether gave a crystalline solid which was filtered and dried in vacuo giving a solid, 15.5 g, 92% yield.

$^1$H NMR (400 MHz, CDCl$_3$): δ7.25–7.9 (m, 8 H), 3.78 (s, 3 H).

EXAMPLE 1E 4-(3,5-Dimethoxy-phenyl)-2-(2-trifluoromethyl-phenyl)-1,1-dioxo-1,2-dihydro-1λ$^6$-benzo[e][1,2]thiazine-3-carboxylic Acid Methyl Ester 1. Preparation of 3,5-dimethoxy-phenyl-boronic Acid 3,5-Dimethoxychlorobenzene (14.0 g, 81 mmol) in 10 mL of THF was added dropwise into a refluxing solution of 2.5 g (100 mmol) of Mg turning in 15 mL of THF with 2 drops of dibromoethane. After the addition, the reaction mixture was refluxed for 48 hours. The Grignard solution was then added into a solution of 40.0 g (380 mmol) of trimethyl borate in 300 mL of THF at 0° C., stirring at room temperature overnight. The reaction solution was diluted with 1N HCl (400 mL) and ethyl acetate (300 mL). The organic layer was separated and was washed with 1N HCl (50 mL), water, brine, dried with MgSO$_4$, concentrated down, and recrystallized in ethyl acetate and ether to give 3.15 g (17.5 mmol, 22% yield) boronic acid.

$^1$HNMR (300 MHz, CDCl$_3$): δ6.48 (s, 1H), 5.14 (b, 2H), 6.96 (s, 2H).

2. Preparation of 4-(3,5-dimethoxy-phenyl)-2-(2-trifluoromethyl-phenyl)-1,1-dioxo-1,2-dihydro-1λ$^6$-benzo[e][1,2]thiazine-3-carboxylic Acid Methyl Ester (1E)

To dimethylformamide (18 mL) was added 1,1-dioxo-4-(trifluoromethanesulfonyloxy)-2-(2-trifluoromethyl-phenyl)-1,2-dihydro-1λ$^6$-benzo[e][1,2]thiazine-3-carboxylic acid methyl ester, (1.60 g, 3.0 mmol), palladium tetrakis(triphenyl phosphine) (0.2 g, 0.17 mmol), potassium carbonate (0.7 g. 6.0 mmol), 2-methoxy-phenyl-boronic acid (0.88 g, 6.0 mmol), and toluene (50 mL). The mixture was heated to 100° C. for 30 minutes and was filtered through a pad of Celite. The filtrate and EtOAc washing solution was washed three times with saturated sodium bicarbonate solution, brine, and dried over charcoal and anhydrous magnesium sulfate. The suspension was filtered and stripped to an oil which was resuspended in ethyl acetate and ethyl ether. Insoluble material from this mixture was filtered off, and the filtrate was concentrated in vacuo to an oil. The residue was chromatographed on silica gel eluted with a mixture of ethyl acetate and hexane (25:75). The appropriate fractions were concentrated in vacuo and crystallized from ethyl ether giving a solid 1.29 g, 83% yield.

Analysis calculated for C$_{25}$H$_{20}$F$_3$N$_1$O$_6$S$_1$: C, 57.80; H, 3.88; N, 2.70; Found: C. 57.56; H, 3.86; N, 2.66.

MS: m/e 519 (M$^+$)

EXAMPLE 1

4-(3,5-Dimethoxy-phenyl)-2-(2-trifluoromethyl-phenyl)-1,1-dioxo-1,2-dihydro-1λ$^6$-benzo[e][1,2]thiazine-3-carboxylic Acid The solution of 4-(3,5-dimethoxy-phenyl)-2-(2-trifluoromethyl-phenyl)-1,1-dioxo-1,2-dihydro-1λ$^6$-benzo[e][1,2]thiazine-3-carboxylic acid methyl ester (1.29 g, 2.5 mmol) and lithium hydroxide monohydrate (0.3 g 12.5 mmol) in 30 mL of MeOH and 15 mL water was refluxed for 2.5 hours and evaporated to an oil. The residue was dissolved in water, washed with ethyl ether, and the aqueous layer decanted. The aqueous layer was acidified to pH 1 with concentrated HCl and extracted into ethyl ether, washed with brine, dried over anhydrous magnesium sulfate, filtered, and evaporated to a foam. The residue was chromatographed on 50 g silica gel eluted with chloroform, and the appropriate fractions were concentrated in vacuo and evaporated from ethyl ether giving a solid foam. 1.4 g, 66% yield. NMR spectra and elemental analysis were consistent with the structure.

MS: m/e 505 (M$^+$)

EXAMPLE 2A 2-(2-Chloro-phenylsulfamoyl)-benzoic Acid Methyl Ester

Prepared in the same way as illustrated in Example 1A in 28% yield. The NMR spectra and elemental analysis were consistent with the structure.

EXAMPLE 2B

2-[(2-Chloro-phenyl)-methoxycarbonylmethyl-sulfamoyl]-benzoic Acid Methyl Ester

Prepared in the same way as illustrated in Example 1B in 84% yield. The NMR spectra and elemental analysis were consistent with the structure.

EXAMPLE 2C 2-(2-Chloro-phenyl)-4-hydroxy-1,1-dioxo-1,2-dihydro-1λ$^6$-benzo[e][1,2]thiazine-3-carboxylic Acid Methyl Ester Prepared in the same way as illustrated in Example 1C in 77% yield. The NMR spectra and elemental analysis were consistent with the structure.

EXAMPLE 2D 2-(2-Chloro-phenyl)-1,1-dioxo-4-(trifluoro-methanesulfonyloxy)-1,2-dihydro-1λ$^6$-benzo[e][1,2]thiazine-3-carboxylic Acid Methyl Ester Prepared in the same way as illustrated in Example 1D in 75% yield. The NMR spectra and elemental analysis were consistent with the structure.

EXAMPLE 2E 2-(2-Chloro-phenyl)-4-(7-methoxy-benzo[1,3]dioxol-5-yl)-1,1-dioxo-1,2-dihydro-1λ$^6$-benzo[e][1,2]thiazine-3-carboxylic Acid Methyl Ester Prepared in the same way as illustrated in Example 1E in 88% yield. The NMR spectra and elemental analysis were consistent with the structure.

MS: m/z 485 (M$^+$)

EXAMPLE 2

2-(2-Chloro-phenyl)-4-(3,5-dimethoxy-phenyl)-1,1-dioxo-1,2-dihydro-1λ$^6$-benzo[e][1,2]thiazine-3-carboxylic Acid Prepared in the same way as illustrated in Example 1 in 99% yield. The NMR spectra and elemental analysis were consistent with the structure.

MS: m/z 471 (M$^+$)

EXAMPLE 3A 2-(2-Bromo-phenylsulfamoyl)-benzoic Acid Methyl Ester

Prepared in the same way as illustrated in Example 1A in 81% yield. The NMR spectra and elemental analysis were consistent with the structure.

EXAMPLE 3B

2-[(2-Bromo-phenyl)-methoxycarbonylmethyl-sulfamoyl]-benzoic Acid Methyl Ester

Prepared in the same way as illustrated in Example 1B in 76% yield. The NMR spectra and elemental analysis were consistent with the structure.

EXAMPLE 3C 2-(2-Bromo-phenyl)-4-hydroxy-1,1-dioxo-1,2-dihydro-1λ$^6$-benzo[e][1,2]thiazine-3-carboxylic Acid Methyl Ester Prepared in the same way as illustrated in Example 1C in 58% yield. The NMR spectra and elemental analysis were consistent with the structure.

EXAMPLE 3D 2-(2-Bromo-phenyl)-1,1-dioxo-4-(trifluoro-methanesulfonyloxy)-1,2-dihydro-1λ$^6$-benzo[e][1,2]thiazine-3-carboxylic Acid Methyl Ester Prepared in the same way as illustrated in Example 1D in 75% yield. The NMR spectra and elemental analysis were consistent with the structure.

EXAMPLE 3E 2-(2-Bromo-phenyl)-4-(3,5-dimethoxy-phenyl)-1,1-dioxo-1,2-dihydro-1λ$^6$-benzo[e][1,2]thiazine-3-carboxylic Acid Methyl Ester Prepared in the same way as illustrated in Example 1E in 88% yield. The NMR spectra and elemental analysis were consistent with the structure.

EXAMPLE 3

2-(2-Bromo-phenyl)-4-(3,5-dimethoxy-phenyl)-1,1-dioxo-1,2-dihydro-1λ$^6$-benzo[e][1,2]thiazine-3-carboxylic Acid Prepared in the same way as illustrated in Example 1 in 81% yield. The NMR spectra and elemental analysis were consistent with the structure.

MS: m/z 471 (M$^+$)

EXAMPLE 4E 2-(2-Chloro-phenyl)-4-(7-methoxy-benzo[1,3]dioxol-5-yl)-1,1-dioxo-1,2-dihydro-1λ$^6$-benzo[e][1,2]thiazine-3-carboxylic Acid Methyl Ester 1. Preparation of (1-Bromo-3,4-methylenedioxy-5-methoxybenzene)

To dimethylformamide (400 mL) was added 1-bromo-3,4-dihydroxy-5-methoxybenzene (40 g, 182 mmol), potassium carbonate (75.7 g, 548 mmol), and dibromomethane (95.2 g, 548 mmol), followed by heating to reflux for 1 hour. The solvent was evaporated in vacuo, and the residue was taken up into ethyl ether, filtered, washed with saturated potassium carbonate solution, brine, 1N citric acid solution, and brine. The organic phase was dried over anhydrous magnesium sulfate and filtered through charcoal. The filtrate was concentrated in vacuo giving a crystalline precipitate which was filtered, washed with hexane, and dried in vacuo to a solid. This material was distilled at 2 mm Hg, 125° C., giving a crystalline solid, 21.7 g, 52% yield. NMR spectra and elemental analysis were consistent with the structure.

2. Preparation of (4-Methoxy-1,3-benzodioxol-6-yl Boronic Acid)

To tetrahydrofuran (40 mL) was added magnesium turnings (2.33 g, 95.8 mmol), 1-bromo-3,4-methylenedioxy-5-methoxybenzene (21.7 g, 93.9 mmol) and a catalytic amount of iodine. Following vigorous reaction, the metal was consumed, and the solution was added to a solution of trimethylborate (38 mL, 334 mmol) in tetrahydrofuran (100 mL) at −78° C. over 45 minutes. The mixture was stirred at −78° C. for an additional 2 hours, then at 25° C. overnight. To the mixture was added 1N HCl (200 mL) followed by stirring at 25° C. for 3 days. The solvent was removed in vacuo, and the suspension was extracted with ethyl ether. The ether phase was washed with brine, and the product was extracted into 0.5N NaOH. The NaOH solution was washed with ethyl ether and acidified to pH 1 with 2N HCl. The acidified aqueous phase was extracted with ethyl ether, washed with brine, dried over anhydrous magnesium sulfate, filtered, and evaporated to a brown solid, 7.43 g, 40% yield. The material was of sufficient purity to be used in subsequent preparations.

3. Example 4E was prepared in the same way as illustrated in Example 1E in 85% yield. The NMR spectra and elemental analysis were consistent with the structure.

EXAMPLE 4

2-(2-Chloro-phenyl)-4-(7-methoxy-benzo[1,3]dioxol-5-yl)-1,1-dioxo-1,2-dihydro-1λ$^6$-benzo[e][1,2]thiazine-3-carboxylic Acid Prepared in the same way as illustrated in Example 1 in 67% yield. The NMR spectra and elemental analysis were consistent with the structure.

EXAMPLE 5A 2-(2-Benzyl-phenylsulfamoyl)-benzoic Acid Methyl Ester

Prepared in the same way as illustrated in Example 1A in 43% yield. The NMR spectra and elemental analysis were consistent with the structure.

EXAMPLE 5B 2-(2-Benzyl-phenyl)-methoxycarbonylmethyl-
sulfamoyl)-benzoic Acid Methyl Ester Prepared in the same way as illustrated in Example 1B in 67% yield. The NMR spectra and elemental analysis were consistent with the structure.

EXAMPLE 5C 2-(2-Benzyl-phenyl)-4-hydroxy-1,1-dioxo-1,2-
dihydro-1$\lambda^6$-benzo[e][1,2]thiazine-3-carboxylic
Acid Methyl Ester Prepared in the same way as illustrated in Example 1C in 87% yield. The NMR spectra and elemental analysis were consistent with the structure.

EXAMPLE 5D 2-(2-Benzyl-phenyl)-1,1-dioxo-4-(trifluoro-
methanesulfonyloxy)-1,2-dihydro-1$\lambda^6$-benzo[e][1,2]
thiazine-3-carboxylic Acid Methyl Ester Prepared in the same way as illustrated in Example 1D in 85% yield. The NMR spectra and elemental analysis were consistent with the structure.

EXAMPLE 5E 2-(2-Benzyl-phenyl)-4-(7-methoxy-benzo[1,3]
dioxol-5-yl)-1,1-dioxo-1,2-dihydro-1$\lambda^6$-benzo[e][1,
2]thiazine-3-carboxylic Acid Methyl Ester Prepared in the same way as illustrated in Example 1E in 50% yield. The NMR spectra and elemental analysis were consistent with the structure.

EXAMPLE 5

2-(2-Benzyl-phenyl)-4-(7-methoxy-benzo[1,3]
dioxol-5-yl)-1,1-dioxo-1,2-dihydro-1$\lambda^6$-benzo[e][1,
2]thiazine-3-carboxylic Acid Prepared in the same way as illustrated in Example 1 in 54% yield. The NMR spectra and elemental analysis were consistent with the structure.

Analysis calculated for $C_{30}H_{23}N_1O_7S_1$ $(H_2O)_{1.75}$: C, 60.55; H, 4.32; N, 2.35; Found: C, 60.76; H, 4.37; N, 2.29.

EXAMPLE 6A 2-(2,6-Dimethyl-phenylsulfamoyl)-benzoic Acid
Methyl Ester

Prepared in the same way as illustrated in Example 1A in 50% yield. The NMR spectra and elemental analysis were consistent with the structure.

EXAMPLE 6B

2-[(2,6-Dimethyl-phenyl)-methoxycarbonylmethyl-
sulfamoyl]-benzoic Acid Methyl Ester Prepared in the same way as illustrated in Example 1B in 88% yield. The NMR spectra and elemental analysis were consistent with the structure.

EXAMPLE 6C 2-(2,6-Dimethyl-phenyl)-4-hydroxy-1,1-dioxo-1,2-
dihydro-1$\lambda^6$-benzo[e][1,2]-thiazine-3-carboxylic
Acid Methyl Ester Prepared in the same way as illustrated in Example 1C in 87% yield. The NMR spectra and elemental analysis were consistent with the structure.

EXAMPLE 6D 2-(2,6-Dimethyl-phenyl)-1,1-dioxo-4-(trifluoro-
methanesulfonyloxy)-1,2-dihydro-1$\lambda^6$-benzo[e][1,2]
thiazine-3-carboxylic Acid Methyl Ester Prepared in the same way as illustrated in Example 1D in 94% yield. The NMR spectra and elemental analysis were consistent with the structure.

EXAMPLE 6E 2-(2,6-Dimethyl-phenyl)-4-(7-methoxy-benzo[1,3]
dioxol-5-yl)-1,1-dioxo-1,2-dihydro-1$\lambda^6$-benzo[e][1,
2]thiazine-3-carboxylic Acid Methyl Ester Prepared in the same way as illustrated in Example 1E in 58% yield. The NMR spectra and elemental analysis were consistent with the structure.

EXAMPLE 6

2-(2,6-Dimethyl-phenyl)-4-(7-methoxy-benzo[1,3]
dioxol-5-yl)-1,1-dioxo-1,2-dihydro-1$\lambda^6$-benzo[e][1,
2]thiazine-3-carboxylic Acid Monosodium Salt To dioxane (15 mL) was added 2-(2,6-dimethyl-phenyl)-4-(7-methoxy-benzo[1,3]dioxol-5-yl)-1,1-dioxo-1,2-dihydro-1$\lambda^6$-benzo[e][1,2]thiazine-3-carboxylic acid methyl ester, (0.99 g, 2.01 mmol) and a solution of lithium hydroxide monohydrate (0.42 g, 10 mmol) in 15 mL water. The mixture was heated at 90° C. for 18 hours, filtered, and evaporated to a solid. The residue was dissolved in water and ethyl ether and the aqueous layer decanted. The aqueous layer was acidified to pH 1 with concentrated HCl and extracted into ethyl ether, washed with brine, dried over anhydrous magnesium sulfate, filtered, and evaporated to a white solid, 1.05 g. To methanol (20 mL) was added this solid (0.63 g, 1.32 mmol), followed by 0.985N NaOH (1.34 mL, 0.683 mmol). The mixture was evaporated to a glassy solid, redissolved in 30 mL water, and filtered at 45$\mu$. The filtrate was lyophilized to a white solid, 0.65 g. NMR spectra was consistent with the structure. Elemental analysis was consistent for the structure as a hydrate, holding an additional 1.75 mol of water.

Analysis calculated for $C_{25}H_{20}N_1O_7S_1Na(H_2O)_{1.75}$: C, 56.10; H, 4.32; N, 2.53; S. 5.91; Na, 4.09; $H_2O$, 5.68. % Found: C, 56.33; H, 4.44; N, 2.62; S, 6.02; Na, 4.31; $H_2O$, 5.91.

EXAMPLE 7E 4-(7-Methoxy-benzo[1,3]dioxol-5-yl)-1,1-dioxo-2-
(2-trifluoromethyl-phenyl)-1,2-dihydro-1$\lambda^6$-benzo[e]
[1,2]thiazine-3-carboxylic Acid Methyl Ester Prepared in the same way as illustrated in Example 1E in 75% yield. The NMR spectra and elemental analysis were consistent with the structure.

EXAMPLE 7

4-(7-Methoxy-benzo[1,3]dioxol-5-yl)-1,1-dioxo-2-
(2-trifluoromethyl-phenyl)-1,2-dihydro-1$\lambda^6$-benzo[e]
[1,2]thiazine-3-carboxylic Acid Prepared in the same way as illustrated except using dioxane as solvent in Example 1E in 66% yield. The NMR spectra and elemental analysis were consistent with the structure. The acid (0.495 g, 0.953 mmol) was dissolved in 10 mL of MeOH and was treated with 0.985N NaOH (0.967 mL, 0.953 mmol). The mixture was evaporated to a glassy solid, redissolved in 50 mL water and filtered at 45μ. The filtrate was lyophilized to a white solid, 0.502 g. NMR spectra was consistent with the structure. Elemental analysis was consistent for the structure as a hydrate, holding an additional 1.75 mol of water.

Analysis calculated for $C_{24}H_{15}N_1O_7S_1Na(H_2O)_{1.75}$: % Theory: C, 49.52; H, 3.05; N, 2.30; S, 5.54; Na, 3.93; $H_2O$, 5.30; F, 10.23. % Found: C, 50.31; H, 3.25; N, 2.44; S, 5.60; Na, 4.01; $H_2O$, 5.50; F, 9.94.

Following illustrate the preparation in Scheme 3.

EXAMPLE 8M

2-[Hydroxy-(7-methoxy-benzo[1,3]dioxol-5-yl)-methyl]-N-o-tolyl-benzenesulfonamide To tetrahydrofuran (200 mL) was added N-o-tolyl-benzenesulfonamide (4.95 g, 20 mmol). After cooling to −72° C. a solution of n-butyllithium (1.6 M, 25 mL in hexane) was added, and the mixture was stirred for 3 hours at −72° C. A solution of 3-methoxy-4,5-methylenedioxybenzaldehyde (3.60 g, 20 mmol) in tetrahydrofuran (70 mL) was added, and the mixture was stirred and warmed to 0° C. over 1.5 hours. The mixture was poured into 200-mL saturated ammonium chloride solution, and the organic phase was decanted. The solvent was evaporated in vacuo and the residue was suspended in ethyl ether, washed with saturated sodium bicarbonate and brine solutions. The solution was dried over anhydrous magnesium sulfate, filtered, and evaporated to give a syrup which was chromatographed on 500 g silica gel eluted with a mixture of ethyl acetate and hexane (35:65). The appropriate fractions were concentrated in vacuo and crystallized giving a solid, 4.15 g, 48.6% yield, mp 155–158° C. NMR spectra and elemental analysis were consistent with the structure.

EXAMPLE 8N ({2-[Hydroxy-(7-methoxy-benzo[1,3]dioxol-5-yl)-methyl]-benzenesulfonyl}-o-tolyl-amino)-acetic Acid Methyl Ester Sixty percent sodium hydride suspension in oil (0.422 g, 10.55 mmol) was washed with tetrahydrofuran and was added to tetrahydrofuran (175 mL). To this was added 2-[hydroxy-(7-methoxy-benzo[1,3]dioxol-5-yl)-methyl]-N-o-tolyl-benzenesulfonamide (4.1 g, 9.59 mmol). After stirring for 30 minutes, methyl bromoacetate (1.09 mL, 11.5 mmol) was added followed by stirring at reflux for 18 hours. The mixture was evaporated to an oil in vacuo, and the residue was resuspended in ethyl ether, washed with 1N citric and brine. The solution was dried over anhydrous magnesium sulfate, filtered, and evaporated to a solid. The material was chromatographed on 300 g silica gel eluted with a mixture of ethyl acetate and hexane (35:65). The appropriate fractions were concentrated in vacuo from ethyl ether giving a solid, 4.29 g, 89.5% yield. NMR spectra and elemental analysis were consistent with the structure.

EXAMPLE 8O

{[2-(7-Methoxy-benzo[1,3]dioxole-5-carbonyl)-benzenesulfonyl]-o-tolyl-amino}-acetic Acid Methyl Ester To acetone (225 mL) was added ({2-[hydroxy-(7-methoxy-benzo[1,3]dioxol-5-yl)-methyl]-benzenesulfonyl}-o-tolyl-amino)-acetic acid methyl ester (4.17 g, 8.35 mmol), and 8N Jones reagent (4 mL). The mixture was stirred 15 minutes giving a suspended solid. Isopropanol (20 mL) was added followed by stirring for 15 minutes. The mixture was filtered, saturated sodium bicarbonate solution was added, and the solvent was removed in vacuo giving a paste. The paste was resuspended in ethyl acetate and water, filtered, and washed with saturated sodium bicarbonate, brine and dried over anhydrous magnesium sulfate. The solution was filtered and evaporated to a solid which was crystallized from ethyl acetate and ethyl ether giving a white solid, 2.41 g, 59% yield, mp 159–170° C. NMR spectra and elemental analysis were consistent with the structure.

EXAMPLE 8E 4-(7-Methoxy-benzo[1,3]dioxol-5-yl)-1,1-dioxo-2-o-tolyl-1,2-dihydro-1λ$^6$-benzo[e][1,2]thiazine-3-carboxylic Acid Methyl Ester To a dry 100-mL flask was added {[2-(7-methoxy-benzo[1,3]dioxole-5-carbonyl)-benzenesulfonyl]-o-tolyl-amino}-acetic acid methyl ester (2.0 g, 4.2 mmol), dry 4 angstrom molecular sieves (8 g), and Ti(TfO)$_2$Cl$_2$ (0.56 g, 0.48 mmol). The flask was cooled to −60° C. and dichloromethane (45 mL) was added. A solution of triethylamine (1.35 g, 9.73 mmol) in dichloromenthan (18 mL) was added. The mixture was warmed to 5° C. over 2 hours, followed by refrigeration at 0° C. for 18 hours. The mixture was poured in to 50-mL ammonium phosphate buffer solution (pH 7), stirred 20 minutes, and filtered. The organic phase was washed with brine, dried over anhydrous magnesium sulfate, filtered, and evaporated in vacuo to an oil. The oil was chromatographed on 150 g silica gel eluted with a mixture of ethyl acetate and hexane (40:60). The appropriate fractions were evaporated in vacuo, and the residue was evaporated to a foam, 1.02 g, 53%. NMR spectra and elemental analysis were consistent with the structure.

EXAMPLE 8

4-(7-Methoxy-benzo[1,3]dioxol-5-yl)-1,1-dioxo-2-o-tolyl-1,2-dihydro-1λ$^6$-benzo[e][1,2]thiazine-3-carboxylic Acid To dioxane (10 mL) was added 4-(7-methoxy-benzo[1,3]dioxol-5-yl)-1,1-dioxo-2-o-tolyl-1,2-dihydro-1λ$^6$-benzo[e][1,2]thiazine-3-carboxylic acid methyl ester (0.72 g, 1.49 mmol) and a solution of lithium hydroxide monohydrate (0.374 g, 8.9 mmol) in 6 mL water. The mixture was heated at 80° C. for 1.5 hours, filtered, and evaporated to a solid. The residue was dissolved in water and ethyl ether and the aqueous layer decanted. The aqueous layer was acidified to pH 1 with concentrated HCl and extracted into ethyl ether, washed with brine, dried over anhydrous magnesium sulfate, filtered, and evaporated to a solid, 0.70 g. The material was chromatographed on 15 g silica gel eluted with chloroform. The appropriate fractions were combined and evaporated in vacuo from ethyl ether giving a solid, 0.272 g. NMR spectra was consistent with the structure. Elemental analysis was consistent for the structure as a hydrate, holding an additional 0.25 moles of water.

Analysis calculated for $C_{24}H_{19}N_1O_7S_1$ $(H_2O)_{0.25}$: % Theory: C, 61.11; H, 4.33; N, 2.84; S, 6.74; $H_2O$, 0.43. % Found: C, 61.33; H, 4.18; N, 2.98; S, 6.82; $H_2O$, 0.96.

EXAMPLE 9E 2-(2-Bromo-phenyl)-4-(7-methoxy-benzo[1,3]
dioxol-5-yl)-1,1-dioxo-1,2-dihydro-1$\lambda^6$-benzo[e][1,
2]thiazine-3-carboxylic Acid Methyl Ester This example was prepared according to Scheme 1a.

1. Preparation of (1-bromo-3,4-methylenedioxy-5-methoxybenzene)

To dimethylformamide (400 mL) was added 1-bromo-3,4-dihydroxy-5-methoxybenzene (40 g, 182 mmol), potassium carbonate (75.7 g, 548 mmol), and dibromomethane (95.2 g, 548 mmol), followed by heating to reflux for 1 hour. The solvent was evaporated in vacuo, and the residue was taken up into ethyl ether, filtered, washed with saturated potassium carbonate solution, brine, 1N citric acid solution, and brine. The organic phase was dried over anhydrous magnesium sulfate and filtered through charcoal. The filtrate was concentrated in vacuo giving a crystalline precipitate which was filtered, washed with hexane, and dried in vacuo to a solid. This material was distilled at 2 mm Hg, 125° C., giving a crystalline solid, 21.7 g, 52% yield. NMR spectra and elemental analysis were consistent with the structure.

2. To tetrahydrofuran (30 mL) was added 1-bromo-3,4-methylenedioxy-5-methoxybenzene (1.25 g, 5.41 mmol). After cooling to −72° C., a solution of n-butyllithium (1.6 M in hexane, 3.54 mL) was added. After stirring for 45 minutes, a solution of zinc bromide (1.27 g, 5.69 mmol) in tetrahydrofuran (20 mL) was added, and the mixture was stirred at −72° C. for 45 minutes, followed by warming to −25° C. To this mixture was added 2-(2-bromo-phenyl)-1,1-dioxo-4-(trifluoro-methanesulfonyloxy)-1,2-dihydro-1$\lambda^6$-benzo[e][1,2]thiazine-3-carboxylic acid methyl ester and (1.48 g, 2.80 mmol), palladium tetrakis(triphenyl phosphine) (1.30 g, 1.05 mmol). The mixture was heated to reflux for 1 hour and was evaporated in vacuo to a paste. The mixture was resuspended in ethyl acetate, washed with 1N citric acid solution, brine, filtered, and dried over anhydrous magnesium sulfate. The suspension was filtered and stripped to an oil which was partially crystallized from ethyl ether giving a solid. The solid was chromatographed on 50 g silica gel eluted with a mixture of ethyl acetate and hexane (20:80). The appropriate fractions were concentrated in vacuo and crystallized from ethyl ether. These solids were combined with those recovered from the initial crystallization and were in vacuo giving a solid, 0.836 g, 28% yield. NMR spectra and elemental analysis were consistent with the structure.

EXAMPLE 9

2-(2-Bromo-phenyl)-4-(7-methoxy-benzo[1,3]
dioxol-5-yl)-1,1-dioxo-1,2-dihydro-1$\lambda^6$-benzo[e][1,
2]thiazine-3-carboxylic Acid Monosodium Salt To dioxane (20 mL) was added 2-(2-bromo-phenyl)-4-(7-methoxy-benzo[1,3]dioxol-5-yl)-1,1-dioxo-1,2-dihydro-1$\lambda^6$-benzo[e][1,2]thiazine-3-carboxylic acid methyl ester, (0.75 g, 1.38 mmol) and a solution of lithium hydroxide monohydrate (0.28 g, 6.74 mmol) in 8 mL water. The mixture was heated at 80° C. for 2 hours and evaporated to an oil. The residue was dissolved in water, washed with ethyl ether, and the aqueous layer decanted. The aqueous layer was acidified to pH 1 with 6N HCl and extracted into ethyl ether, washed with brine, dried over anhydrous magnesium sulfate, filtered, and evaporated to a yellow solid. To methanol (4 mL) was added the solid (0.652 g, followed by 0.985N NaOH (1.22 mL). The mixture was evaporated to a glassy solid, redissolved in 30 mL water, and filtered at 45 microns. The filtrate was lyophilized to a white solid, 0.65 g. NMR spectra was consistent with the structure. Elemental analysis was consistent for the structure as a hydrate, holding an additional 1.25 mol of water.

Analysis calculated for $C_{23}H_{15}N_1O_7S_1Br_1(H_2O)_{1.25}$: % Theory: C, 47.78; H, 3.03; N, 2.40; S, 5.23; Na, 4.12; $H_2O$, 3.81; Br, 13.23. % Found: C, 48.05; H, 3.07; N, 2.44; S, 5.58; Na, 4.00; $H_2O$, 3.92; Br, 13.90.

EXAMPLE 10E 4-(7-Ethyl-benzo[1,3]dioxol-5-yl)-1,1-dioxo-2-(2-
trifluoromethyl-phenyl)-1,2-dihydro-1$\lambda^6$-benzo[e][1,
2]thiazine-3-carboxylic Acid Methyl Ester This example was prepared according to Scheme 1a.

a. Preparation of 5-bromo-2,3-dihydroxy-benzaldehyde

To dichloromethane (400 mL) was added 5-bromo-2-hydroxy-3-methoxy-benzaldehyde (prepared per *Synthetic Communications*, 1991;21(8,9):1091–5; 94.6 g, 409.4 mmol). To this was added with cooling to 10° C. a solution of boron tribromide (153.9 g, 614 mmol) in dichloromethane (400 mL) over 20 minutes, followed by warming to 25° C. overnight. The mixture was poured into 2 L of ice and extracted with chloroform. The chloroform solution was washed with brine, dried over anhydrous magnesium sulfate, and filtered. The filtrate was concentrated in vacuo and hexane was added giving a crystalline precipitate which was filtered, washed with hexane, and dried in vacuo to a solid, 80.0 g, 90% yield. NMR spectra and elemental analysis were consistent with the structure.

b. Preparation of 6-bromo-benzo[1,3]dioxole-4-carbaldehyde

Dimethylformamide, 750 mL, was purged with dry nitrogen gas and 5-bromo-2,3-dihydroxy-benzaldehyde (83 g, 382 mmol) was added. To the solution was added potassium carbonate (158 g, 1.14 mol) followed by diiodomethane (306 g, 1.14 mol). The mixture was warmed to 85° C. for 2.5 hours, and evaporated in vacuo to an oil. The mixture was partitioned between ethyl acetate and water and filtered through celite. The phases were separated, and the organic phase was washed with brine, dried over anhydrous magnesium sulfate, filtered, and evaporated to a small volume causing a solid to precipitate. The solid was filtered, washed with 50:50 hexane/ethyl acetate, and set aside. Three more crops of solid were subsequently isolated in this manner from the filtrate. The solids were combined and dried in vacuo giving a beige solid, 69.45 g, 79.4% yield. NMR spectra and elemental analysis were consistent with the structure.

c. Preparation of 1-(6-bromo-benzo[1,3]dioxol-4-yl)-ethanol

To 150 mL tetrahydrofuran, was added 6-bromo-benzo[1,3]dioxole-4-carbaldehyde (15 g, 65.4 mmol). To the solution was added a solution of methyl magnesium bromide (1.0 M) in di-n butyl ether (72 mL) followed by exotherm and solid formation. The mixture was stirred at 25° C. for 2.5 hours and evaporated in vacuo to a solid. The mixture was suspended in ethyl acetate washed with 1N citric acid, brine, and dried over anhydrous magnesium sulfate. The mixture was filtered and evaporated to an oil. The oil was induced to crystallize from ethyl acetate and hexane giving a white solid which was filtered and dried in vacuo giving a solid, 10.48 g, 65.4% yield. NMR spectra and elemental analysis were consistent with the structure.

d. Preparation of 1-(6-bromo-4-ethyl-benzo[1,3]dioxole

To a 250-mL flask was added 1-(6-bromo-benzo[1,3]dioxol-4-yl)-ethanol (9.3 g, 37.9 mmol) was added. The solid was cooled to −50° C. and trifluoroacetic acid (44 mL, 568 mmol) was added. Followed addition of triethylsilane (60.5 mL, 379 mmol). The mixture was stirred at reflux for 5 hours, and evaporated in vacuo to an oil. The oil was distilled twice, collecting the fraction boiling between 80° C. and 110° C. at 1.5 mm Hg. The oil was chromatographed on 100 g silica gel, eluted with 5:95 ethyl acetate/hexane. Evaporation of the appropriate fractions gave a clear oil, 6.56 g, 75.6% yield. NMR spectra and elemental analysis were consistent with the structure.

e. Alternate Preparation of 1-(6-bromo-4-ethyl-benzo[1,3]dioxole

Preparation of 5-bromo-2,3-dihydroxyethylbenzene

A 2 L flask was charged with tetrahydrofuran (600 mL) and one normal aqueous sodium hydroxide (260 mL). To this solution was added 5-bromo-3-ethylsalicylaldehyde (58 g, 0.25 mol, prepared by the procedure described by S. A. Weerawarna et al., *J. Het. Chem.*, 1991 ;28: 1400). With good stirring, hydrogen peroxide (400 mL of 3% solution, 0.35 mol) was slowly added. After 30 minutes, tlc (silica plate eluted with hexane:ethyl acetate, 7:3) showed no more starting material. The reaction mixture was brought to a pH of ~5.0 by addition of acetic acid. The tetrahydrofuran was removed under vacuum, then the aqueous mixture was extracted twice with 300 mL portions of methyl t-butyl ether. The ether solution was dried over magnesium sulfate, filtered, and concentrated to a dark oil (54.8 g). This material was not further purified, but used directly in the next reaction.

Preparation of 1-(6-bromo-4-ethyl-benzo[1,3]dioxole

A 2 L, 3 neck round bottom flask was equipped with an overhead stirrer, heating mantle, condenser, and nitrogen inlet. The flask was flushed with nitrogen and charged with acetonitrile (700 mL), followed by 5-bromo- 2,3-dihydroxyethylbenzene (54.5 g, assumed to be 0.25 mol), then anhydrous cesium carbonate (121 g, 0.37 mol) and bromochloromethane (57 g, 0.44 mol). The mixture was stirred and heated to reflux (~74° C.). At that point, sodium iodide (5 g, 0.03 mol) was added, and the mixture was boiled for 90 minutes. The mixture was then cooled and filtered with suction. The filter cake was rinsed with acetonitrile, then the solvent was removed under vacuum. The residue was treated with water (700 mL), and the mixture was extracted twice with 400 mL portions of hexane. The hexane was removed under vacuum, then the residue (~36 g) was distilled under high vacuum. The distillate, collected at a head temperature of 84° C. (0.8 mm Hg) weighed 24 g (0.10 mol, 41% for the two steps). The product thus obtained has NMR characteristics consistent with the title compound and is greater than 95% pure by gas chromatography.

f. Preparation of 10E

To tetrahydrofuran (30 mL) was added (6-bromo-4-ethyl-benzo[1,3]dioxole) (1.24 g, 5.41 mmol). After cooling to −78° C., a solution of n-butyllithium (1.6 M in hexane, 3.54 mL) was added. After stirring for 45 minutes, a solution of anhydrous zinc bromide (1.27 g, 5.69 mmol) in tetrahydrofuran (20 mL) was added, and the mixture was stirred at −72° C. for 45 minutes, followed by warming to −25° C. To this mixture was added 1,1-dioxo-4-(trifluoro-methanesulfonyloxy)-2-(2-trifluoromethyl-phenyl)-1,2-dihydro-1$\lambda^6$-benzo[e][1,2]thiazine-3-carboxylic acid methyl ester (1.49 g, 2.80 mmol), and palladium tetrakis (triphenyl phosphine) (1.30 g, 1.05 mmol). The mixture was heated to 70° C. for 2.5 hours and was evaporated in vacuo to an oil. The mixture was resuspended in ethyl acetate, washed with 1N citric acid solution, brine, filtered, and dried over anhydrous magnesium sulfate. The suspension was filtered and stripped to an oil which was partially crystallized from ethyl ether giving a solid. The filtrate was concentrated in vacuo and was chromatographed on 50 g silica gel eluted with a mixture of ethyl acetate and hexane (30:70). The appropriate fractions were concentrated in vacuo and crystallized from ethyl ether. These solids were combined with those recovered from the initial crystallization and were dried in vacuo giving a solid, 0.836 g, 53% yield. NMR spectra and elemental analysis were consistent with the structure.

EXAMPLE 10

4-(7-Ethyl-benzo[1,3]dioxol-5-yl)-1,1-dioxo-2-(2-trifluoromethyl-phenyl)-1,2-dihydro-1$\lambda^6$-benzo[e][1,2]thiazine-3-carboxylic Acid, Sodium Salt To dioxane (15 mL) was added 4-(7-ethyl-benzo[1,3]dioxol-5-yl)-1,1-dioxo-2-(2-trifluoromethyl-phenyl)-1,2-dihydro-1$\lambda^6$-benzo[e][1,2]thiazine-3-carboxylic acid methyl ester, (0.7 g, 1.32 mmol) and a solution of lithium hydroxide monohydrate (0.28 g, 6.58 mmol) in 15 mL water. The mixture was heated at reflux for 2.5 hours and evaporated to a solid. The residue was dissolved in water, filtered, and washed with ethyl ether and the organic layer decanted. The aqueous layer was acidified to pH 1 with 6N HCl and extracted into ethyl ether, washed with brine, dried over anhydrous magnesium sulfate, filtered, and evaporated to a yellow foam, 0.51 g. To methanol (4 mL) was added the solid (0.465 g), followed by 0.985N NaOH (0.91 mL). The mixture was evaporated to a glassy solid, redissolved in 30 mL water, and filtered at 45 i. The filtrate was lyophilized to a white solid, 0.448 g, 70% yield. NMR spectra was consistent with the structure. Elemental analysis was consistent for the structure as a hydrate, holding an additional 1.5 moles of water.

Analysis calculated for $C_{25}H_{18}N_1O_6SF_3Na(H_2O)_{1.5}$, MWT 566.46: C, 51.82; H, 3.41; N, 2.35; S, 6.13; F, 9.79; Na, 4.06; $H_2O$, 4.53. Found: C, 53.00; H, 3.56; N, 2.47; S, 5.66; F, 10.06; Na, 4.05; $H_2O$, 4.77.

The free acid 10 (32.1 g, 62 mmol) was dissolved in 100 mL of MeOH. To this was added 62 mL of 1N KOH. After stirring at room temperature for 1 hour, most of the MeOH was removed by rotatory evaporator. EtOH was then added (250 mL), and the solution was stirred for a while at 60° C. Then 30 mL of isopropyl alcohol (IPA) was added, and the mixture was cooled to room temperature for 2 hours. The precipitate was collected by filtration and was washed with some portions of cold IPA. The product was dried in vacuum at 45° C. overnight.

Analysis calculated for $C_{25}H_{17}F_3N_1O_6S_1K_1$ $(H_2O)_{0.15}$: C, 53.79; H, 3.12; N, 2.51. Found: C, 53.75; H, 2.84; N, 2.41.

EXAMPLE 11E

4-Benzo[1,3]dioxol-5-yl-1,1-dioxo-2-(2-trifluoromethyl-phenyl)-1 2-dihydro-1$\lambda^6$-benzo[e][1,2]thiazine-3-carboxylic Acid Methyl Ester Prepared in the same way as illustrated in Example 1E in 95% yield. The NMR spectra and elemental analysis were consistent with the structure.

EXAMPLE 11

4-Benzo[1,3]dioxol-5-yl-1,1-dioxo-2-(2-trifluoromethyl-phenyl)-1,2-dihydro-1$\lambda^6$-benzo[e][1,2]thiazine-3-carboxylic Acid Prepared in the same way as illustrated in Example 1E in 98% yield. The NMR spectra and elemental analysis were consistent with the structure.

MS m/z 489 ($M^+$)

The following procedures are illustrated in Scheme 2.

EXAMPLE 12A 2-o-Tolylsulfamoyl-benzoic Acid Methyl Ester

A solution of 22.24 g (85.3 mmol) of 90% methyl-2-(chlorosulfonyl)-benzoate in $CH_2Cl_2$ was treated with 7.6 mL (93.8 mmol, 1.1 eq) of pyridine, 10.01 mL (93.8 mmol, 1.1 eq) of amine, and 3.47 g (28.4 mmol, 0.33 eq) of DMAP. The reaction mixture was then stirred overnight at room temperature under $N_2$. The solvent was concentrated to one-third volume, diluted with ethyl acetate, washed with 1N HCl, brine, dried over $MgSO_4$, and evaporated. Crystallization from Hex/EtOAc afforded the product as 19.50 g of orange cubes, 75% yield.

Analysis calculated for $C_{15}H_{15}N_1O_4$: C, 59.00; H, 4.95; N, 4.59. Found: C, 59.02; H, 4.69; N, 4.35.

EXAMPLE 12H 2-(6-Methyl-benzo[1,3]dioxol-5-yl)-1,1-dioxo-1,2-dihydro-1$\lambda^6$-benzo[d]isothiazol-3-one A solution of 16.15 g (53.0 mmol) of 12A, 4.28 mL (53.0 mmol, 1.0 eq) of pyridine, and 2.15 g (17.6 mmol, 0.33 eq) of DMAP in 150 mL of xylenes was heated to reflux overnight, cooled to room temperature, treated with 1N HCl, and allowed to stir for 2 hours. The ppt solid was collected, washed with 1N HCl, water, and xylenes, then air dried overnight under high house vacuum to give the product as 8.20 g of white solid, 57% yield.

MS(CI) m/e: 273 ($M^+$)

EXAMPLE 12I

3-[2-(6-Methyl-benzo[1,3]dioxol-5-ylsulfamoyl) phenyl]3-oxo-propionic Acid tert-Butyl Ester $KN(TMS)_2$, 95%, 16.6 g (78.8 mmol, 3 eq), was dissolved in 175 mL of dry THF and cooled to −78° C. This was treated with 10.6 mL (78.8 mmol, 3 eq) of t-butylacetate and the reaction mixture stirred for 30 minutes at −78° C. To this was added 7.18 g (26.3 mmol) of 12H, in portions over 40 minutes, the reaction mixture stirred for 4 hours at −78° C., then quenched with saturated aqueous $NH_4Cl$ and allowed to come slowly to room temperature overnight. The mixture was treated with 1N HCl, stirred for 1 hour, then extracted with EtOAc. The organic portion was washed with water, brine, dried over $MgSO_4$, and evaporated. The oil was purified on a silica gel column eluted with $CHCl_3$ to give the product as an orange oil which solidified upon standing, 70% yield.

MS(CI) m/e: 334 ($M^+$-t-Bu)

EXAMPLE 12J

2-Bromo-3-[2-(2-methyl-phenylsulfamoyl)-phenyl]-3-oxo-propionic Acid tert-Butyl Ester A solution of 5.47 g (14.0 mmol) of 12I in 80 mL of $CCl_4$ was treated with 2.50 g (14.0 mmol, 1.0 eq) of NBS and 0.1 g (0.04 mmol) of benzoyl peroxide and the reaction mixture heated to reflux for 5 hours, cooled to room temperature, passed through a plug of silica gel, washed with $CCl_4$, and evaporated. The crude product was obtained as an orange oil after attempts to purify it by column chromatography, 64% crude yield. The NMR is consistent with the structure.

EXAMPLE 12K 2-(6-Methyl-benzo[1,3]dioxol-5-yl)-4-hydroxy-1,1-dioxo-1,2-dihydro-1$\lambda^6$-benzo[e][1,2]thiazine-3-carboxylic Acid tert-Butyl Ester A solution of 4.24 g (9.06 mmol) of the crude brominated product in DMF was treated with 3.13 g (22.6 mmol, 2 eq) of $K_2CO_3$ and stirred overnight at room temperature. The solution was diluted with 1N HCl, the ppt'd solid collected, washed with water, and dried. The solid was dissolved in ether, dried over $MgSO_4$, filtered, and evaporated. The impure foam was dried overnight under high vacuum, then treated with Hex/EtOAc 2:1 to afford the product as a white solid, 26% yield.

MS(CI) m/e: 387 ($M^+$)

EXAMPLE 12L

4-Benzo[1,3]dioxol-5-yl-2-(6-methyl-benzo[1,3]dioxol-5-yl)-1,1-dioxo-1,2-dihydro-1$\lambda^6$-benzo[e][1,2]thiazine-3-carboxylic Acid tert-Butyl Ester The triflate was prepared according to procedures described in Example 1D. Then, a solution of 1.14 g (4.39 mmol) of the crude triflate in toluene/DMF (10 mL/3 mL) was treated with 0.55 g (3.29 mmol, 1.5 eq) of boronic acid, 0.45 g (3.29 mmol, 1.5 eq) of $K_2CO_3$, and 0.25 g (0.2 mmol, 0.1 eq) of $Pd(PPh_3)_4$, and the reaction mixture heated to reflux for 2 hours. Cooled to room temperature, diluted with ethyl acetate, extracted with saturated aqueous $NaHCO_3$, and the organic portion washed with brine, dried over $MgSO_4$, and evaporated. The dark oil was purified on a silica gel column eluted with Hex/EtOAc 2:1, then on a silica gel column eluted with $CHCl_3$. Drying afforded the product as 0.62 g of white foam; 57% yield.

MS(APCI) m/e: 492 ($M^+$)

EXAMPLE 12

4-Benzo[1,3]dioxol-5-yl-2-(6-methyl-benzo[1,3]dioxol-5-yl)-1,1-dioxo-1,2-dihydro-1λ$^6$-benzo[e][1,2]thiazine-3-carboxylic Acid A solution of 0.49 g (0.1 mmol) of the above mentioned Example 12L in $CH_2Cl_2$ was treated with 1 mL of trifluoroacetic acid and the reaction mixture stirred overnight at room temperature. The volume was concentrated, diluted with ether, washed with water (3×), brine, dried over $MgSO_4$, and evaporated. The foam was dried under high vacuum, dissolved in ether, and extracted with 1N NaOH/ $H_2O$. The aqueous portions were acidified with 1N HCl, extract with ether, washed with brine, dried over $MgSO_4$, and evaporated. The foam was taken up in $CHCl_3$, evaporated, and dried under high vacuum at 72° C. This process afforded the product as a light yellow foam.

MS(ES) m/e: 435 (M$^+$)

EXAMPLE 13A

2-(2-Ethyl-phenylsulfamoyl)-benzoic Acid Methyl Ester

Prepared in the same way as illustrated in Example 1A in 49% yield.

Analysis calculated for $C_{16}H_{17}N_1O_4S_1$: %C 60.17; %H 5.37; %N 4.39. Found: %C 60.12; %H 5.27; %N 4.32.

MS(ES) m/e: 319 (M$^+$)

EXAMPLE 13B

2-[(2-Ethyl-phenyl)-methoxycarbonylmethyl-sulfamoyl]-benzoic Acid Methyl Ester Prepared in the same way as illustrated in Example 1B in 58% yield.

Analysis calculated for $C_{19}H_{21}N_1O_6S_1$: %C, 58.30; %H, 5.41; %N, 3.58. Found: %C, 58.27; %H, 5.17; %N, 3.51.

MS(ES) m/e: 391 (M$^+$)

EXAMPLE 13C

2-(2-Ethyl-phenyl)-4-hydroxy-1,2-dioxo-1,2-dihydro-1λ$^6$-benzo[e][1,2]thiazine-3-carboxylic Acid Methyl Ester Prepared in the same way as illustrated in Example 1C in 81% yield. The NMR spectra and elemental analysis were consistent with the structure.

MS(ES) m/e: 359 (M$^+$)

EXAMPLE 13D

2-(2-Ethyl-phenyl)-1,1-dioxo-4-(trifluoro-methanesulfonyloxy)-1,2-dihydro-1λ$^6$-benzo[e][1,2]thiazine-3-carboxylic Acid Methyl Ester Prepared in the same way as illustrated in Example 1D in 98% yield. The NMR spectra is consistent with the structure.

EXAMPLE 13E

4-Benzo[1,3]dioxol-5-yl-2-(2-ethyl-phenyl)-1,1-dioxo-1,2-dihydro-1λ$^6$-benzo[e][1,2]thiazine-3-carboxylic Acid Methyl Ester Prepared in the same way as illustrated in Example 1E in 81% yield.

Analysis calculated for $C_{25}H_{21}N_1O_6S_1$: %C, 64.78; %H, 4.57; %N, 3.02. Found: %C, 64.6; %H, 4.44; %N, 2.87.

EXAMPLE 13

4-Benzo[1,3]dioxol-5-yl-2-(2-ethyl-phenyl)-1,1-dioxo-1,2-dihydro-1λ$^6$-benzo[e][1,2]thiazine-3-carboxylic Acid Prepared in the same way as illustrated in Example 1 in 65% yield.

Analysis calculated for $C_{24}H_{19}N_1O_6S_1$: %C, 64.13; %H, 4.26; %/N, 3.12. Found: %C, 63.45; %H, 4.02; %N, 3.02.

MS(ES) m/e: 404 (M$^+$-COOH)

EXAMPLE 14A

2-(2-Propyl-phenylsulfamoyl)-benzoic Acid Methyl Ester

Prepared in the same way as illustrated in Example 1A in 71% yield.

MS(CI) m/e: 333 (M$^+$)

EXAMPLE 14B

2-[(2-Propyl-phenyl)-methoxycarbonylmethyl-sulfamoyl]-benzoic Acid Methyl Ester Prepared in the same way as illustrated in Example 1B in 91% yield.

Analysis calculated for $C_{19}H_{21}N_1O_6S_1$: %C, 58.30; %H, 5.41; %N, 3.58. Found: %C, 58.27; %H, 5.17; %N, 3.51.

MS(APCI) m/e: 406 (M$^+$+1)

EXAMPLE 14C

2-(2-Propyl-phenyl)-4-hydroxy-1,1-dioxo-1,2-dihydro-1λ$^6$-benzo[e][1,2]thiazine-3-carboxylic Acid Methyl Ester Prepared in the same way as illustrated in Example 1C in 74% yield. The NMR spectra and elemental analysis were consistent with the structure.

MS(APCI) m/e: 374 (M$^+$+1)

EXAMPLE 14E

4-Benzo[1,3]dioxol-5-yl-2-(2-propyl-phenyl)-1,1-dioxo-1,2-dihydro-1λ$^6$-benzo[e][1,2]thiazine-3-carboxylic Acid Methyl Ester The triflate was prepared in the same way as illustrated in Example 1D and the coupling reaction was run in the same way as illustrated in Example 1E with crude 14D in 72% overall yield. The NMR spectra and elemental analysis were consistent with the structure.

EXAMPLE 14

4-Benzo[1,3]dioxol-5-yl-2-(2-propyl-phenyl)-1,1-dioxo-1,2-dihydro-1λ$^6$-benzo[e][1,2]thiazine-3-carboxylic Acid Prepared in the same way as illustrated in Example 1 in 96% yield.

Analysis calculated for $C_{25}H_{21}N_1O_6S_1$: %C, 64.78; %H, 4.57; %N, 3.02. Found: %C, 64.51; %H, 4.81; %N, 2.89.

EXAMPLE 15A 2-(2-Isopropyl-phenylsulfamoyl)-benzoic Acid Methyl Ester

Prepared in the same way as illustrated in Example 1A in 76% yield.

MS(CI) m/e: 333 ($M^+$)

EXAMPLE 15B

2-[(2-Isopropyl-phenyl)-methoxycarbonylmethyl-sulfamoyl]-benzoic Acid Methyl Ester Prepared in the same way as illustrated in Example 1B in 77% yield.

MS(APCI) m/e: 406 ($M^+$+1)

EXAMPLE 15C 2-(2-Isopropyl-phenyl)-4-hydroxy-1,1-dioxo-1,2-dihydro-1$\lambda^6$-benzo[e][1,2]thiazine-3-carboxylic Acid Methyl Ester Prepared in the same way as illustrated in Example 1C in 65% yield. The NMR spectra and elemental analysis were consistent with the structure.

MS(APCI) m/e: 373 ($M^+$)

EXAMPLE 15E

4-Benzo[1,3]dioxol-5-yl-2-(2-isopropyl-phenyl)-1,1-dioxo-1,2-dihydro-1$\lambda^6$-benzo[e][1,2]thiazine-3-carboxylic Acid Methyl Ester The triflate was prepared in the same way as illustrated in Example 1D and the coupling reaction was run in the same way as illustrated in Example 1E in 63% overall yield.

MS(APCI) m/e: 477 ($M^+$)

EXAMPLE 15

4-Benzo[1,3]dioxol-5-yl-2-(2-isopropyl-phenyl)-1,1-dioxo-1,2-dihydro-1$\lambda^6$-benzo[e][1,2]thiazine-3-carboxylic Acid Prepared in the same way as illustrated in Example 1 in 99% yield.

Analysis calculated for $C_{25}H_{21}N_1O_6S_1$: %C, 64.78; %H, 4.57; %N, 3.02. Found: %C, 64.73; %H, 4.76; %N, 2.77.

EXAMPLE 16A 2-(2-Butyl-phenylsulfamoyl)-benzoic Acid Methyl Ester

Prepared in the same way as illustrated in Example 1A in 44% yield. The NMR spectra and elemental analysis were consistent with the structure.

EXAMPLE 16B

2-[(2-Butyl-phenyl)-methoxycarbonylmethyl-sulfamoyl]-benzoic Acid Methyl Ester

Prepared in the same way as illustrated in Example 1B. The crude product was carried to the next step without purification.

MS(ES) m/e: 419 ($M^+$−1)

EXAMPLE 16C 2-(2-Butyl-phenyl)-4-hydroxy-1,1-dioxo-1,2-dihydro-1$\lambda^6$-benzo[e][1,2]thiazine-3-carboxylic Acid Methyl Ester Prepared in the same way as illustrated in Example 1C in 55% overall yield.

Analysis calculated for $C_{20}H_{21}N_1O_5S_1$: %C, 62.00; %H, 5.46; %N, 3.62. Found: %C, 61.78; %H, 5.57; %N, 3.48.

MS(ES) m/e: 386 ($M^+$−1)

EXAMPLE 16D 2-(2-Butyl-phenyl)-1,1-dioxo-4-(trifluoro-methanesulfonyloxy)-1,2-dihydro-1$\lambda^6$-benzo[e][1,2]thiazine-3-carboxylic Acid Methyl Ester Prepared in the same way as illustrated in Example 1D in 88% yield. The NMR spectra is consistent with the structure.

EXAMPLE 16E

4-Benzo[1,3]dioxol-5-yl-2-(2-butyl-phenyl)-1,1-dioxo-1,2-dihydro-1$\lambda^6$-benzo[e][1,2]thiazine-3-carboxylic Acid Methyl Ester Prepared in the same way as illustrated in Example 1E in 59% yield.

Analysis calculated for $C_{27}H_{25}N_1O_6S_1$: %C, 65.92; %H, 5.15; %N, 2.84. Found: %C, 65.84; %H, 5.32; %N, 2.70.

MS(ES) m/e:491 ($M^+$)

EXAMPLE 16

4-Benzo[1,3]dioxol-5-yl-2-(2-butyl-phenyl)-1,1-dioxo-1,2-dihydro-1$\lambda^6$-benzo[e][1,2]thiazine-3-carboxylic Acid Prepared in the same way as illustrated in Example 1 in 26% yield.

MS(CI) m/e: 459 ($M^+$−OH)

The following procedures are illustrated in Scheme 2.

EXAMPLE 17A 2-(2-Bromo-phenylsulfamoyl)-benzoic Acid Methyl Ester

Prepared in the same way as illustrated in Example 12A in 79% yield.

MS(CI) m/e: 369 ($M^+$)

EXAMPLE 17H 2-(2-Bromo-phenyl)-1,1-dioxo-1,2-dihydro-1$\lambda^6$-benzo[d]isothiazol-3-one Prepared in the same way as illustrated in Example 12H in 56% yield.

MS(CI) m/e: 338 ($M^+$)

EXAMPLE 17I

3-[2-(2-Bromo-phenylsulfamoyl)phenyl]3-oxo-propionic Acid tert-Butyl Ester

Prepared in the same way as illustrated in Example 12I in quantitative yield and was carried to the next step without purification.

EXAMPLE 17J

2-Bromo-3-[2-(2-bromo-phenylsulfamoyl)-phenyl]-3-oxo-propionic Acid tert-Butyl Ester Prepared in the same way as illustrated in Example 12J in quantitative yield and was carried to the next step without purification.

EXAMPLE 17K 2-(2-Bromo-phenyl)-4-hydroxy-1,1-dioxo-1,2-dihydro-1$\lambda^6$-benzo[e][1,2]thiazine-3-carboxylic Acid tert-Butyl Ester Prepared in the same way as illustrated in Example 12K in 68% yield.

MS(CI) m/e: 451 (M$^+$)

EXAMPLE 17L

4-Benzo[1,3]dioxol-5-yl-2-(2-bromo-phenyl)-1,1-dioxo-1,2-dihydro-1$\lambda^6$-benzo[e][1,2]thiazine-3-carboxylic Acid tert-Butyl Ester The triflate was prepared according to procedures described in Example 1D. The coupling reaction was carried out in the same way as illustrated in Example 12L in 57% yield.

MS(APCI) m/e: 556 (M$^+$)

EXAMPLE 17

4-Benzo[1,3]dioxol-5-yl-2-(2-bromo-phenyl)-1,1-dioxo-1,2-dihydro-1$\lambda^6$-benzo[e][1,2]thiazine-3-carboxylic Acid Prepared in the same way as illustrated in Example 12 as a yellow foam.

Analysis calculated for $C_{22}H_{14}Br_1N_1O_6S_1$: %C, 52.81; %H, 2.82; %N, 2.80. Found: %C, 52.69; %H, 2.68; %N, 2.55.

EXAMPLE 18A 2-(2-Chloro-phenylsulfamoyl)-benzoic Acid Methyl Ester

Prepared in the same way as illustrated in Example 12A in 92% yield.

MS(CI) m/e: 325 (M$^+$)

EXAMPLE 18H 2-(2-Chloro-phenyl)-1,1-dioxo-1,2-dihydro-1$\lambda^6$-benzo[d]isothiazol-3-one Prepared in the same way as illustrated in Example 12H in 52% yield.

MS(CI) m/e: 294 (M$^+$)

EXAMPLE 18I

3-[2-(2-Chloro-phenylsulfamoyl)phenyl]3-oxo-propionic Acid tert-Butyl Ester

Prepared in the same way as illustrated in Example 12I in quantitative yield and was carried to the next step without purification.

MS(CI) m/e: 354 (M$^+$-t-Bu)

EXAMPLE 18J

2-Bromo-3-[2-(2-chloro-phenylsulfamoyl)-phenyl]-3-oxo-propionic Acid tert-Butyl Ester Prepared in the same way as illustrated in Example 12J in quantitative yield and was carried to the next step without purification.

MS(CI) m/e: 352 (M$^+$-t-Bu-Br)

EXAMPLE 18K 2-(2-Chloro-phenyl)-4-hydroxy-1,1-dioxo-1,2-dihydro-1$\lambda^6$-benzo[e][1,2]thiazine-3-carboxylic Acid tert-Butyl Ester Prepared in the same way as illustrated in Example 12K in 57% yield.

MS(CI) m/e: 407 (M$^+$)

EXAMPLE 18L

4-Benzo[1,3]dioxol-5-yl-2-(2-chloro-phenyl)-1,1-dioxo-1,2-dihydro-1$\lambda^6$-benzo[e][1,2]thiazine-3-carboxylic Acid tert-Butyl Ester The triflate was prepared according to procedures described in Example 1D. The coupling reaction was carried out in the same way as illustrated in Example 12L in 68% yield.

MS(APCI) m/e: 512 (M$^+$)

EXAMPLE 18

4-Benzo[1,3]dioxol-5-yl-2-(2-chloro-phenyl)-1,1-dioxo-1,2-dihydro-1$\lambda^6$-benzo[e][1,2]thiazine-3-carboxylic Acid Prepared in the same way as illustrated in Example 12 in 71% yield.

MS(ES) m/e: 456 (M$^+$)

EXAMPLE 19A 2-(2-Fluoro-phenylsulfamoyl)-benzoic Acid Methyl Ester

Prepared in the same way as illustrated in Example 1A in 82% yield.

MS(CI) m/e: 309 (M$^+$)

EXAMPLE 19B

2-[(2-Fluoro-phenyl)-methoxycarbonylmethyl-sulfamoyl]-benzoic Acid Methyl Ester

Prepared in the same way as illustrated in Example 1B in 93% yield.

MS(APCI) m/e: 382 (M$^+$)

EXAMPLE 19C 2-(2-Fluoro-phenyl)-4-hydroxy-1,1-dioxo-1,2-dihydro-1λ⁶-benzo[e][1,2]thiazine-3-carboxylic Acid Methyl Ester Prepared in the same way as illustrated in Example 1C in 33% yield.

MS(APCI) m/e: 350 (M⁺)

EXAMPLE 19D 2-(2-Fluoro-phenyl)-1,1-dioxo-4-(trifluoro-methanesulfonyloxy)-1,2-dihydro-1λ⁶-benzo[e][1,2]thiazine-3-carboxylic Acid Methyl Ester Prepared in the same way as illustrated in Example 1D in 84% yield. The NMR spectra is consistent with the structure.

EXAMPLE 19E

4-Benzo[1,3]dioxol-5-yl-2-(2-fluoro-phenyl)-1,1-dioxo-1,2-dihydro-1λ⁶-benzo[e][1,2]thiazine-3-carboxylic Acid Methyl Ester Prepared in the same way as illustrated in Example 1E in 91% yield.

MS(CI) m/e: 453 (M⁺)

EXAMPLE 19

4-Benzo[1,3]dioxol-5-yl-2-(2-fluoro-phenyl)-1,1-dioxo-1,2-dihydro-1λ⁶-benzo[e][1,2]thiazine-3-carboxylic Acid Prepared in the same way as illustrated in Example 1 in 23% yield.

MS(CI) m/e: 439 (M⁺)

EXAMPLE 20A 2-(2-Benzyloxy-phenylsulfamoyl)-benzoic Acid Methyl Ester

Prepared in the same way as illustrated in Example 1A in 95% yield. The NMR spectra and elemental analysis were consistent with the structure.

EXAMPLE 20B

2-[(2-Benzyloxy-phenyl)-methoxycarbonylmethyl-sulfamoyl]-benzoic Acid Methyl Ester Prepared in the same way as illustrated in Example 1B in 89% yield. The NMR spectra and elemental analysis were consistent with the structure.

EXAMPLE 20C 2-(2-Benzyloxy-phenyl)-4-hydroxy-1,1-dioxo-1,2-dihydro-1λ⁶-benzo[e][1,2]thiazine-3-carboxylic Acid Methyl Ester Prepared in the same way as illustrated in Example 1C in 89% yield. The NMR spectra and elemental analysis were consistent with the structure.

EXAMPLE 20D 2-(2-Benzyloxy-phenyl)-1,1-dioxo-4-(trifluoro-methanesulfonyloxy)-1,2-dihydro-1λ⁶-benzo[e][1,2]thiazine-3-carboxylic Acid Methyl Ester Prepared in the same way as illustrated in Example 1D in 97% yield. The NMR spectra and elemental analysis were consistent with the structure.

EXAMPLE 20E

4-Benzo[1,3]dioxol-5-yl-2-(2-hydroxy-phenyl)-1,1-dioxo-1,2-dihydro-1λ⁶-benzo[e][1,2]thiazine-3-carboxylic Acid Methyl Ester The coupling reaction was carried out with 20D and the corresponding boronic acid in the same way as illustrated in Example 1E in 80% yield. The product was dissolved in DMF and was treated with 20% Pd/C under 50 atm pressure for 2 days to obtain 20E in 20% yield and recovery of the rest as the starting material. The NMR spectra and elemental analysis were consistent with the structure.

EXAMPLE 20

4-Benzo[1,3]dioxol-5-yl-2-(2-hydroxy-phenyl)-1,1-dioxo-1,2-dihydro-1λ⁶-benzo[e][1,2]thiazine-3-carboxylic Acid Prepared in the same way as illustrated in Example 1 in 99% yield. The NMR spectra and elemental analysis were consistent with the structure.

MS: m/z 471 (M⁺)

EXAMPLE 21A 2-(2,3-Dichloro-phenylsulfamoyl)-benzoic Acid Methyl Ester

Prepared in the same way as illustrated in Example 1A in 80% yield. The NMR spectra is consistent with the structure.

EXAMPLE 21B

2-[(2,3-Dichloro-2-phenyl)-methoxycarbonylmethyl-sulfamoyl]-benzoic Acid Methyl Ester Prepared in the same way as illustrated in Example 1B in 52% yield. The NMR spectra is consistent with the structure.

EXAMPLE 21C 2-(2,3-Dichloro-2-phenyl)-4-hydroxy-1,2-dioxo-1,2-dihydro-1λ⁶-benzo[e][1,2]thiazine-3-carboxylic Acid Methyl Ester Prepared in the same way as illustrated in Example 1C in 59% yield. The NMR spectra is consistent with the structure.

EXAMPLE 21D 2-(2,3-Dichloro-phenyl)-1,1-dioxo-4-(trifluoro-methanesulfonyloxy)-1,2-dihydro-1λ⁶-benzo[e][1,2]thiazine-3-carboxylic Acid Methyl Ester Prepared in the same way as illustrated in Example 1D in 100% yield. The NMR spectra is consistent with the structure.

EXAMPLE 21E

4-Benzo[1,3]dioxol-5-yl-2-(2,3-dichloro-phenyl)-1,1-dioxo-1,2-dihydro-1λ⁶-benzo[e][1,2]thiazine-3-carboxylic Acid Methyl Ester Prepared in the same way as illustrated in Example 1E in 65% yield. The NMR spectra is consistent with the structure.

EXAMPLE 21

4-Benzo[1,3]dioxol-5-yl-2-(2,3-dichloro-phenyl)-1,1-dioxo-1,2-dihydro-1λ⁶-benzo[e][1,2]thiazine-3-carboxylic Acid Prepared in the same way as illustrated in Example 1 in 100% yield.

MS: m/z 489 (M⁺)

EXAMPLE 22A

2-(2,4-Dichloro-phenylsulfamoyl)-benzoic Acid Methyl Ester

Prepared in the same way as illustrated in Example 1A in 55% yield.

Analysis calculated for $C_{14}H_{11}Cl_2N_1O_4S_1$: %C, 46.48; %H, 3.08; %N, 3.89. Found: %C, 46.65; %H, 2.85; %N, 3.87.

EXAMPLE 22B

2-[(2,4-Dichloro-phenyl)-methoxycarbonylmethyl-sulfamoyl]-benzoic Acid Methyl Ester Prepared in the same way as illustrated in Example 1B in 51% yield.

MS(APCI) m/e: 431 (M$^+$)

EXAMPLE 22C

2-(2,4-Dichloro-phenyl)-4-hydroxy-1,1-dioxo-1,2-dihydro-1$\lambda^6$-benzo[e][1,2]thiazine-3-carboxylic Acid Methyl Ester Prepared in the same way as illustrated in Example 1C in 75% yield.

Analysis calculated for $C_{16}H_{11}Cl_2N_1O_5S_1$: %C, 48.02; %H, 2.77; %N, 3.50. Found: %C, 47.92; %H, 2.62; %N, 3.43.

EXAMPLE 22D

2-(2,4-Dichloro-phenyl)-1,1-dioxo-4-(trifluoro-methanesulfonyloxy)-1,2-dihydro-1$\lambda^6$-benzo[e][1,2]thiazine-3-carboxylic Acid Methyl Ester Prepared in the same way as illustrated in Example 1D in 83% yield. The NMR spectra is consistent with the structure.

EXAMPLE 22E

4-Benzo[1,3]dioxol-5-yl-2-(2,4-dichloro-phenyl)-1,1-dioxo-1,2-dihydro-1$\lambda^6$-benzo[e][1,2]thiazine-3-carboxylic Acid Methyl Ester Prepared in the same way as illustrated in Example 1E in 68% yield.

Analysis calculated for $C_{23}H_{15}Cl_2N_1O_6S_1$: %C, 54.99; %H, 2.96; %N, 2.79. Found: %C, 54.99; %H, 3.22'%N, 2.60.

MS(CI) m/e: 502 (M$^+$)

EXAMPLE 22

4-Benzo[1,3]dioxol-5-yl-2-(2,4-dichloro-phenyl)-1,1-dioxo-1,2-dihydro-1$\lambda^6$-benzo[e][1,2]thiazine-3-carboxylic Acid Prepared in the same way as illustrated in Example 1 in 89% yield.

Analysis calculated for $C_{22}H_{13}Cl_2N_1O_6S_1$: %C, 53.89; %H, 2.67; %N, 2.86. Found: %C, 53.25; %H, 2.96; %N, 2.68.

MS: m/z 489 (M$^+$)

EXAMPLE 23A

2-(2-Chloro-4-methoxy-phenylsulfamoyl)-benzoic Acid Methyl Ester

Prepared in the same way as illustrated in Example 1A in 53% yield.

MS(CI) m/e: 355 (M$^+$)

EXAMPLE 23B

2-[(2-Chloro-4-methoxy-phenyl)-methoxycarbonylmethyl-sulfamoyl]-benzoic Acid Methyl Ester Prepared in the same way as illustrated in Example 1B in 96% yield.

MS(CI) m/e: 428 (M$^+$)

EXAMPLE 23C

2-(2-Chloro-4-methoxy-phenyl)-4-hydroxy-1,1-dioxo-1,2-dihydro-1$\lambda^6$-benzo[e][1,2]thiazine-3-carboxylic Acid Methyl Ester Prepared in the same way as illustrated in Example 1C in 73% yield.

MS(CI) m/e: 395 (M$^+$)

EXAMPLE 23D

2-(2-Chloro-4-methoxy-phenyl)-1,1-dioxo-4-(trifluoro-methanesulfonyloxy)-1,2-dihydro-1$\lambda^6$-benzo[e][1,2]thiazine-3-carboxylic Acid Methyl Ester Prepared in the same way as illustrated in Example 1D in 99% yield. The NMR spectra is consistent with the structure.

EXAMPLE 23E

4-Benzo[1,3]dioxol-5-yl-2-(2-chloro-4-methoxy-phenyl)-1,1-dioxo-1,2-dihydro-1$\lambda^6$-benzo[e][1,2]thiazine-3-carboxylic Acid Methyl Ester Prepared in the same way as illustrated in Example 1E in 94% yield.

MS(CI) m/e: 499 (M$^+$)

EXAMPLE 23

4-Benzo[1,3]dioxol-5-yl-2-(2-chloro-4-methoxy-phenyl)-1,1-dioxo-1,2-dihydro-1$\lambda^6$-benzo[e][1,2]thiazine-3-carboxylic Acid Prepared in the same way as illustrated in Example 1 in 97% yield.

MS(CI): m/z 486 (M$^+$)

EXAMPLE 24A

2-(3-Chloro-2-methyl-phenylsulfamoyl)-benzoic Acid Methyl Ester

Prepared in the same way as illustrated in Example 1A in 66% yield.

Analysis calculated for $C_{15}H_{14}Cl_1N_1O_4S_1$: %C, 53.02; %H, 4.15; %N, 4.12. Found: %C, 52.80; %H, 3.91; %N, 4.07.

EXAMPLE 24B

2-[(3-Chloro-2-methyl-phenyl)-methoxycarbonylmethyl-sulfamoyl]-benzoic Acid Methyl Ester Prepared in the same way as illustrated in Example 1B in 76% yield.

Analysis calculated for $C_{18}H_{16}Cl_1N_1O_6S_1$: %C, 52.49; %H, 4.41; %N, 3.40. Found: %C, 52.49; %H, 4.41; %N, 3.29.

EXAMPLE 24C 2-(3-Chloro-2-methyl-phenyl)-4-hydroxy-1,1-dioxo-1,2-dihydro-1$\lambda^6$-benzo[e][1,2]thiazine-3-carboxylic Acid Methyl Ester Prepared in the same way as illustrated in Example 1C in 86% yield.

Analysis calculated for $C_{17}H_{14}Cl_2N_1O_5S_1$: %C, 53.13; %H, 3.72; %N, 3.69. Found: %C, 52.85; %H, 3.65; %N, 3.59.

EXAMPLE 24D 2-(3-Chloro-2-methyl-phenyl)-1,1-dioxo-4-(trifluoro-methanesulfonyloxy)-1,2-dihydro-1$\lambda^6$-benzo[e][1,2]thiazine-3-carboxylic Acid Methyl Ester Prepared in the same way as illustrated in Example 1D in 91% yield. The NMR spectra is consistent with the structure.

EXAMPLE 24E

4-Benzo[1,3]dioxol-5-yl-2-(3-chloro-2-methyl-phenyl)-1,1-dioxo-1,2-dihydro-1$\lambda^6$-benzo[e][1,2]thiazine-3-carboxylic Acid Methyl Ester Prepared in the same way as illustrated in Example 1E in 95% yield.

MS(CI) m/e: 483 (M$^+$)

EXAMPLE 24

4-Benzo[1,3]dioxol-5-yl-2-(3-chloro-2-methyl-phenyl)-1,1-dioxo-1,2-dihydro-1$\lambda^6$-benzo[e][1,2]thiazine-3-carboxylic Acid Prepared in the same way as illustrated in Example 1 in 45% yield.

Analysis calculated for $C_{23}H_{16}Cl_1N_1O_6S_1$: %C, 59.59; %H, 4.29; %N, 2.58. Found: %C, 59.69; %H, 4.75; %N, 2.52.

MS: m/z 469 (M$^+$)

EXAMPLE 25A 2-(6-Chloro-benzo[1,3]dioxol-5-ylsulfamoyl)-benzoic Acid Methyl Ester Prepared in the same way as illustrated in Example 12F in 84% yield.

MS(CI) m/e: 370 (M$^+$)

EXAMPLE 25H 2-(6-Chloro-benzo[1,3]dioxol-5-yl)-1,1-dioxo-1,2-dihydro-1$\lambda^6$-benzo[d]isothiazol-3-one Prepared in the same way as illustrated in Example 12H in 66% yield.

MS(CI) m/e: 338 (M$^+$)

EXAMPLE 25I

3-[2-(6-Chloro-benzo[1,3]dioxol-5-ylsulfamoyl)phenyl]3-oxo-propionic Acid tert-Butyl Ester Prepared in the same way as illustrated in Example 12I in 57% yield and was carried to the next step without purification.

MS(CI) m/e: 453 (M$^+$)

EXAMPLE 25J

2-Bromo-3-[2-(6-chloro-benzo[1,3]dioxol-5-ylsulfamoyl)-phenyl]-3-oxo-propionic Acid tert-Butyl Ester Prepared in the same way as illustrated in Example 12J in 47% yield.

EXAMPLE 25K 2-(6-Chloro-benzo[1,3]dioxol-5-yl)-4-hydroxy-1,1-dioxo-1,2-dihydro-1$\lambda^6$-benzo[e][1,2]thiazine-3-carboxylic Acid tert-Butyl Ester Prepared in the same way as illustrated in Example 12K in 82% yield.

MS(CI) m/e: 451 (M$^+$)

EXAMPLE 25L

4-Benzo[1,3]dioxol-5-yl-2-(6-chloro-benzo[1,3]dioxol-5-yl)-1,1-dioxo-1,2-dihydro-1$\lambda^6$-benzo[e][1,2]thiazine-3-carboxylic Acid tert-Butyl Ester The triflate was prepared according to procedures described in Example 1D. The coupling reaction was carried out in the same way as illustrated in Example 12L in 63% yield.

MS(APCI) m/e: 556 (M$^+$)

EXAMPLE 25

4-Benzo[1,3]dioxol-5-yl-2-6-Chloro-benzo[1,3]dioxol-5-yl)-1,1-dioxo-1,2-dihydro-1$\lambda^6$-benzo[e][1,2]thiazine-3-carboxylic Acid Prepared in the same way as illustrated in Example 12 in 71% yield.

MS(ES) m/e: 500 (M$^+$)

EXAMPLE 26A 2-(2,6-Dimethyl-phenylsulfamoyl)-benzoic Acid Methyl Ester

Prepared in the same way as illustrated in Example 1A in 80% yield.

Analysis calculated for $C_{16}H_{17}N_1O_4S_1$: %C, 60.17; %H, 5.37; %N, 4.39. Found: %C, 59.91, %H, 5.32, %N, 4.33.

EXAMPLE 26B

2-[(2,6-Dimethyl-phenyl)-methoxycarbonylmethyl-sulfamoyl]-benzoic Acid Methyl Ester Prepared in the same way as illustrated in Example 1B in 85% yield.

MS(CI) m/e: 392 (M$^+$+1)

EXAMPLE 26C 2-(2,6-Dimethyl-phenyl)-4-hydroxy-1,1-dioxo-1,2-dihydro-1$\lambda^6$-benzo[e][1,2]thiazine-3-carboxylic Acid Methyl Ester Prepared in the same way as illustrated in Example 1C in 56% yield.

MS(CI) m/e: 360 (M$^+$)

EXAMPLE 26E

4-Benzo[1,3]dioxol-5-yl-2-(2,6-dimethyl-phenyl)-1,1-dioxo-1,2-dihydro-1$\lambda^6$-benzo[e][1,2]thiazine-3-carboxylic Acid Methyl Ester The triflate was prepared in the same way as illustrated in Example 1D, and the coupling reaction was carried out in the same way as illustrated in Example 1E in 64% overall yield.

MS(CI) m/e: 463 (M$^+$)

EXAMPLE 26

4-Benzo[1,3]dioxol-5-yl-2-(2,6-dimethyl-phenyl)-1,1-dioxo-1,2-dihydro-1$\lambda^6$-benzo[e][1,2]thiazine-3-carboxylic Acid Prepared in the same way as illustrated in Example 1 in 100% yield.

MS(CI): m/z 448 (M+−1)

EXAMPLE 27A 2-(2-Pyrrol-1-yl-phenylsulfamoyl)-benzoic Acid Methyl Ester

Prepared in the same way as illustrated in Example 1A in 74% yield.

Analysis calculated for $C_{18}H_{16}N_2O_4S_1$: %C, 60.66; %H, 4.53; %N, 7.86. Found: %C, 60.63; %H, 4.40; %N, 7.77.

MS(CI) m/e: 356 (M$^+$)

EXAMPLE 27B

2-[Methoxycarbonylmethyl-(2-pyrrol-1-yl-phenyl)-sulfamoyl]-benzoic Acid Methyl Ester Prepared in the same way as illustrated in Example 1B in 70% yield.

MS(CI) m/e: 365 (M$^+$)

EXAMPLE 27C

4-Hydroxy-1,1-dioxo-2-(2-pyrrol-1-yl-phenyl)-1,2-dihydro-1$\lambda^6$-benzo[e][1,2]thiazine-3-carboxylic Acid Methyl Ester Prepared in the same way as illustrated in Example 1C in 77% yield.

MS(CI) m/e: 496 (M$^+$)

EXAMPLE 27D 1,1-Dioxo-2-(2-pyrrol-1-yl-phenyl)-4-(trifluoro-methanesulfonyloxy)-1,2-dihydro-1$\lambda^6$-benzo[e][1,2]thiazine-3-carboxylic Acid Methyl Ester Prepared in the same way as illustrated in Example 1D in 93% yield. The NMR spectra is consistent with the structure.

EXAMPLE 27E

4-Benzo[1,3]dioxol-5-yl-1,1-dioxo-2-(2-pyrrol-1-yl-phenyl)-1,2-dihydro-1$\lambda^6$-benzo[e][1,2]thiazine-3-carboxylic Acid Methyl Ester Prepared in the same way as illustrated in Example 1E in 80% yield.

MS(CI) m/e: 500 (M$^+$)

EXAMPLE 27

4-Benzo[1,3]dioxol-5-yl-1,1-dioxo-2-(2-pyrrol-1-yl-phenyl)-1,2-dihydro-1$\lambda^6$-benzo[e][1,2]thiazine-3-carboxylic Acid Prepared in the same way as illustrated in Example 1 in 60% yield.

MS: m/z 486 (M$^+$)

EXAMPLE 28A 2-(3,4-Dimethyl-isoxazol-5-ylsulfamoyl)-benzoic Acid Methyl Ester Prepared in the same way as illustrated in Example 1A in 29% yield. The NMR spectra and elemental analysis were consistent with the structure.

EXAMPLE 28B

2-[(3,4-Dimethyl-isoxazol-5-yl)-methoxycarbonylmethyl-sulfamoyl]-benzoic Acid Methyl Ester Prepared in the same way as illustrated in Example 1B in 46% yield. The NMR spectra and elemental analysis were consistent with the structure.

EXAMPLE 28C 2-(3,4-Dimethyl-isoxazol-5-yl)-4-hydroxy-1,1-dioxo-1,2-dihydro-1$\lambda^6$-benzo[e][1,2]thiazine-3-carboxylic Acid Methyl Ester Prepared in the same way as illustrated in Example 1C in 76% yield. The NMR spectra and elemental analysis were consistent with the structure.

EXAMPLE 28D 2-(3,4-Dimethyl-isoxazol-5-yl)-1,1-dioxo-4-(trifluoro-methanesulfonyloxy)-1,2-dihydro-1$\lambda^6$-benzo[e][1,2]thiazine-3-carboxylic Acid Methyl Ester Prepared in the same way as illustrated in Example 1D in 99% yield. The NMR spectra is consistent with the structure.

EXAMPLE 28E

4-Benzo[1,3]dioxol-5-yl-2-(3,4-dimethyl-isoxazol-5-yl)-1,1-dioxo-1,2-dihydro-1$\lambda^6$-benzo[e][1,2]thiazine-3-carboxylic Acid Methyl Ester Prepared in the same way as illustrated in Example 1E in 41% yield. The NMR spectra is consistent with the structure.

EXAMPLE 28

4-Benzo[1,3]dioxol-5-yl-2-(3,4-dimethyl-isoxazol-5-yl)-1,1-dioxo-1,2-dihydro-1$\lambda^6$-benzo[e][1,2]thiazine-3-carboxylic Acid Prepared in the same way as illustrated in Example 1 in 93% yield.

Analysis calculated for $C_{21}H_{16}N_2O_7S_1$ $(H_2O)_{0.81}$: %C, 56.46; %H, 4.22; %N, 5.73; %S, 6.55. Found: %C, 56.49; %H, 4.22; %N, 5.73; %S, 6.55.

EXAMPLE 29E

4-Benzo[1,3]dioxol-5-yl-2-(2-benzyl-phenyl)-1,1-dioxo-1,2-dihydro-1$\lambda^6$benzo[e][1,2]thiazine-3-carboxylic Acid Methyl Ester Prepared in the same way as illustrated in Example 9E in 52% yield. The NMR spectra and elemental analysis were consistent with the structure.

EXAMPLE 29

4-Benzo[1,3]dioxol-5-yl-2-(2-benzyl-phenyl)-1,1-dioxo-1,2-dihydro-1$\lambda^6$-benzo[e][1,2]thiazine-3-carboxylic Acid Prepared in the same way as illustrated in Example 1 in 79% yield. The NMR spectra and elemental analysis were consistent with the structure. Analysis calculated for $C_{29}H_{21}N_1O_6S_1$ $(H_2O)_{2.5}$: C, 60.20; H, 4.35; N, 2.30; Found: C, 59.87; H, 4.25; N, 2.42.

EXAMPLE 30E 4-(6-Methoxy-benzo[1,3]dioxol-5-yl)-1,1-dioxo-2-(2-trifluoromethyl-phenyl)-1,2-dihydro-1$\lambda^6$-benzo[e][1,2]thiazine-3-carboxylic Acid Methyl Ester 5-Methoxy-1,3-benzodioxol-6-yl-boronic acid was prepared in the same way as illustrated in Example 4E in 91% yield. The coupling reaction was carried out in the same way as illustrated in Example 1E in 94% yield.

MS(CI) m/e: 533 (M$^+$)

EXAMPLE 30

4-(6-Methoxy-benzo[1,3]dioxol-5-yl)-1,1-dioxo-2-(2-trifluoromethyl-phenyl)-1,2-dihydro-1$\lambda^6$-benzo[e][1,2]thiazine-3-carboxylic Acid Prepared in the same way as illustrated in Example 1 in 83% yield.

MS(CI) m/e: 501 (M$^+$-H$_2$O)

EXAMPLE 31E 4-(3,5-Dimethyl-phenyl)-2-(2-trifluoromethyl-phenyl)-1,1-dioxo-1,2-dihydro-1$\lambda^6$-benzo[e][1,2]thiazine-3-carboxylic Acid Methyl Ester The coupling reaction was carried out in the same way as illustrated in Example 1E in 46% yield. The NMR spectra is consistent with the structure.

EXAMPLE 31

4-(3 5-Dimethyl-phenyl)-2-(2-trifluoromethyl-phenyl)-1,1-dioxo-1,2-dihydro-1$\lambda^6$-benzo[e][1,2]thiazine-3-carboxylic Acid Prepared in the same way as illustrated in Example 1 in 96% yield. The NMR spectra is consistent with the structure.

What is claimed is:

1. A process for the preparation of a compound of Formula 1

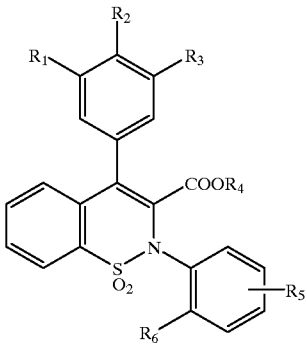

1 or a pharmaceutically acceptable salt thereof wherein $R_1$ is hydrogen, alkyl, or alkoxy;

$R_2$ is hydrogen or alkoxy;

$R_3$ is alkyl or alkoxy;

$R_2$ and $R_3$ may be joined to form a ring

;

$R_4$ is hydrogen or alkyl;

$R_5$ is hydrogen, alkyl, alkoxy, halogen at the 2 or 3, or 4, or 5 positions or $R_5$ is a fused 3,4-methylenedioxy; and $R_6$ is CF$_3$, halogen, alkyl, benzyl, phenyl, hydroxy, or pyrrole comprising:

a) alkylating a compound of formula A

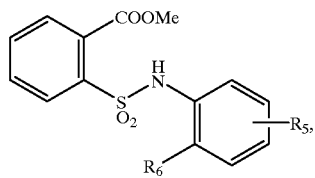

A with sodium hydride in DMF followed by reaction with methyl bromoacetate to produce a compound of formula B

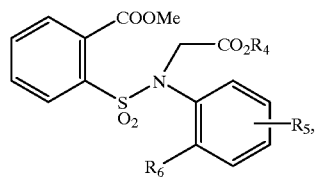

B b) combining compound B in THF with a solution of TiCl$_4$ in solvent at −78° C. and treating with triethylamine and quenching with an acid to produce a compound of formula C

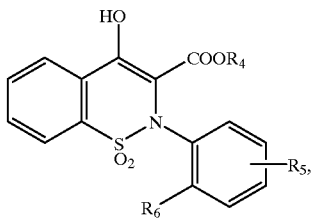

C c) treating compound C with triflic anhydride in a solvent in the presence of pyridine for from 1 to 5 hours to produce a compound of formula

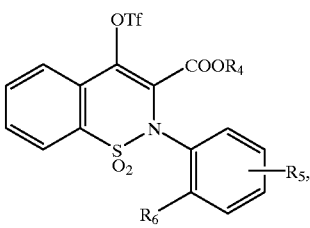

D d) coupling the compound D with a boronic acid of formula X

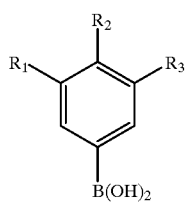

X in DMF and toluene in the presence of a palladium catalyst and potassium carbonate under reflux to produce a compound of Formula 1.

2. A process according to claim 1 wherein in Step b) compound B is treated with $TiCl_2(OTf)_2$ and triethylamine, and quenched with pH 7 phosphate buffer and workup.

3. A process according to claim 1, wherein the compound prepared is a compound of Formula II

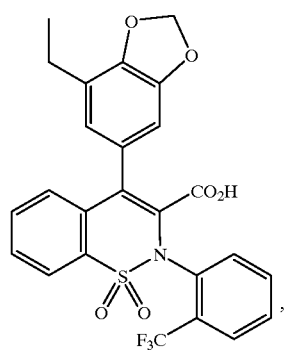

II or a pharmaceutically acceptable salt thereof.

4. A compound named 4-(7-Ethyl-benzo[1,3]dioxol-5-yl)-1,1-dioxo-2-(2-trifluoromethyl-phenyl)-1,2-dihydro-1λ⁶-benzo[e][1,2]thiazine-3-carboxylic acid sodium salt.

5. A compound named 4-(7-Ethyl-benzo[1,3]dioxol-5-yl)-1,1-dioxo-2-(2-trifluoromethyl-phenyl)-1,2-dihydro-1λ⁶benzo[e][1,2]thiazine-3-carboxylic ester potassium salt.

6. 4-(7-Ethyl-benzo[1,3]dioxol-5-yl)-1,1-dioxo-2-(2-trifluoromethyl-phenyl)-1,2-dihydro-1,2-benzo[e][1,2]thiazine-3-carboxylic acid, and pharmaceutically acceptable salts thereof.

7. The compound of claim 6 that is 4-(7-ethyl-benzo[1,3]dioxol-5 -yl)-1,1-dioxo-2-(2-trifluoromethyl-phenyl)-1,2-dihydro-1λ⁶-benzo[e][1,2]thiazine-3-carboxylic acid.

8. A pharmaceutical composition comprising 4-(7-ethyl-benzo[1,3]dioxol-5-yl)-1,1-dioxo-2-(2-trifluoromethyl-phenyl)-1,2-dihydro-1λ⁶-benzo[e][1,2]thiazine-3-carboxylic acid, or a pharmaceutically acceptable salt thereof, in admixture with a pharmaceutically acceptable carrier.

9. A pharmaceutical composition according to claim 8 comprising a compound selected from the group consisting of:

4-(7-ethyl-benzo[1,3]dioxol-5-yl)-1,1-dioxo-2-(2-trifluoromethyl-phenyl)-1,2-dihydro-1λ⁶-benzo[e][1,2]thiazine-3-carboxylic acid sodium salt;

4-(7-ethyl-benzo[1,3]dioxol-5-yl)-1,1-dioxo-2-(2-trifluoromethyl-phenyl)-1,2-dihydro-1λ⁶-benzo[e][1,2]thiazine-3-carboxylic acid potassium salt; and 4-(7-ethyl-benzo[1,3]dioxol-5-yl)-1,1-dioxo-2-(2-trifluoromethyl-phenyl)-1,2-dihydro-1λ⁶-benzo[e][1,2]thiazine-3-carboxylic acid.

10. A pharmaceutical composition according to claim 8 comprising 4-(7-ethyl-benzo[1,3]dioxol-5-yl)-1,1-dioxo-2-(2-trifluoromethyl-phenyl)-1,2-dihydro-1λ⁶-benzo[e][i1,2]thiazine-3-carboxylic acid potassium salt.

11. A method of treating essential, renovascular, malignant, or pulmonary hypertension comprising administering to a host suffering therefrom a therapeutically effective amount of a compound named 4-(7-ethyl-benzo[1,3]dioxol-5-yl)-1,1-dioxo-2-(2-trifluoromethyl-phenyl)-1,2-dihydro-1benzo[e][1,2]thiazine-3-carboxylic acid, or a pharmaceutically acceptable salt thereof.

12. The method according to claim 11 wherein the compound administered is selected from the group consisting of:

4-(7-ethyl-benzo[1,3]dioxol-5-yl)-1,1-dioxo-2-(2-trifluoromethyl-phenyl)-1,2-dihydro-1λ⁶-benzo[e][1,2]thiazine-3-carboxylic acid sodium salt;

4-(7-ethyl-benzo[1,3]dioxol-5-yl)-1,1-dioxo-2-(2-trifluoromethyl-phenyl)-1,2-dihydro-1λ⁶-benzo[e][1,2]thiazine-3-carboxylic acid potassium salt; and 4-(7-ethyl-benzo[1,3]dioxol-5-yl)-1,1-dioxo-2-(2-trifluoromethyl-phenyl)-1,2-dihydro-1λ⁶-benzo[e][1,2]thiazine-3-carboxylic acid.

13. The method according to claim 12 wherein the compound administered is 4-(7-ethyl-benzo[1,3]dioxol-5-yl)-1,1-dioxo-2-(2-trifluoromethyl-phenyl)-1,2-dihydro-1λ⁶-benzo[e][1,2]thiazine-3-carboxylic acid potassium salt.

* * * * *

UNITED STATES PATENT AND TRADEMARK OFFICE
CERTIFICATE OF CORRECTION

PATENT NO.    : 6,265,399 B1
DATED         : July 24, 2001
INVENTOR(S)   : Amy Mae Bunker et al.

It is certified that error appears in the above-identified patent and that said Letters Patent is hereby corrected as shown below:

Column 62,
Line 65, "TiCl$_4$ in solvent at -78°C. and treating with triethy-" should read -- TiCl$_4$ in solvent at -78°C and treating with triethy- --

Column 64,
Line 7, "1$\lambda^6$benzo[e][1,2]thiazine-3-carboxylic ester potassium salt." should read -- 1$\lambda^6$ benzo[e][1,2]thiazine-3-carboxylic acid potassium salt. --
Line 9, "trifluoromethyl-phenyl)-1,2-dihydro-1,2-benzo[e][1,2]" should read
-- trifluoromethyl-phenyl)-1,2-dihydro-1$\lambda^6$-benzo[e][1,2] --
Line 39, "(2-trifluoromethyl-phenyl)-1,2-dihydro-1$\lambda^6$-benzo[e][i1,2]" should read
-- (2-trifluoromethyl-phenyl)-1,2-dihydro-1$\lambda^6$-benzo[e][1,2] --
Line 46, "(dihydro-1benzo[e][1,2]thiazine-3-carboxylic acid, or a" should read
-- (dihydro-1$\lambda^6$-benzo[e][1,2]thiazine-3-carboxylic acid, or a --

Signed and Sealed this

Twenty-ninth Day of October, 2002

*Attest:*

*Attesting Officer*

JAMES E. ROGAN
*Director of the United States Patent and Trademark Office*